US012788602B2

(12) United States Patent
Fleming

(10) Patent No.: US 12,788,602 B2
(45) Date of Patent: Nov. 10, 2026

(54) CABLE BRACE SYSTEM

(71) Applicant: MOBIUS TECHNOLOGIES, LLC, Ketchum, ID (US)

(72) Inventor: Darren Fleming, San Diego, CA (US)

(73) Assignee: Mobius Technologies, LLC, Ketchum, WA (US)

( * ) Notice: Subject to any disclaimer, the term of this patent is extended or adjusted under 35 U.S.C. 154(b) by 0 days.

(21) Appl. No.: 18/365,373

(22) Filed: Aug. 4, 2023

(65) Prior Publication Data

US 2023/0404785 A1 Dec. 21, 2023

Related U.S. Application Data

(63) Continuation of application No. 16/436,786, filed on Jun. 10, 2019, now abandoned, which is a continuation-in-part of application No. 13/867,910, filed on Apr. 22, 2013, now Pat. No. 11,123,210, which is a continuation of application No. 12/987,084, filed on Jan. 8, 2011, now abandoned, which is a continuation-in-part of application No. 11/744,213, filed on May 3, 2007, now abandoned.

(60) Provisional application No. 62/718,529, filed on Aug. 14, 2018, provisional application No. 62/682,560, filed on Jun. 8, 2018.

(51) Int. Cl.
*A61F 5/01* (2006.01)

(52) U.S. Cl.
CPC ............ *A61F 5/0123* (2013.01); *A61F 5/013* (2013.01); *A61F 2005/0137* (2013.01); *A61F 2005/0167* (2013.01); *A61F 2005/0179* (2013.01)

(58) Field of Classification Search
CPC .............. A61F 5/013; A61F 2005/0165; A61F 5/0102; A61F 5/0118; A61F 5/05866; A61F 5/05858; A61F 5/05841; A61F 13/107
See application file for complete search history.

(56) References Cited

U.S. PATENT DOCUMENTS

| | | | |
|---|---|---|---|
| 2,195,024 | A | 3/1940 | Bullock et al. |
| 3,350,719 | A | 11/1967 | Mcclure |
| 3,799,159 | A | 3/1974 | Scott |
| 3,938,509 | A | 2/1976 | Barber |
| 4,864,024 | A | 9/1989 | Sato et al. |
| 4,905,678 | A | 3/1990 | Cumins et al. |
| 4,955,369 | A | 9/1990 | Bledsoe et al. |
| 5,002,045 | A | 3/1991 | Spademan |
| 5,599,288 | A | 2/1997 | Shirley et al. |
| 5,857,988 | A | 1/1999 | Shirley |
| 6,110,138 | A | 8/2000 | Shirley |
| 7,182,740 | B1 | 2/2007 | Castillo |
| 7,198,610 | B2 | 4/2007 | Ingimundarson et al. |
| 7,662,122 | B2 | 2/2010 | Streling |
| 2002/0133108 | A1 | 9/2002 | Jagodzinski |

(Continued)

*Primary Examiner* — Victoria Hicks Fisher
(74) *Attorney, Agent, or Firm* — Richard T. Black; FisherBroyles, LLP

(57) ABSTRACT

It is the object of the invention to provide a bracing system that bolsters the body's natural ligaments to reduce the proneness to injury or re-injury. The invention is a cable system that acts much like the body's natural ligaments, and that resists the forces that cause excessive joint movement and injury. As the ligament travels through the range of motion the control loops formed by cables provide external hyperextension, bending, and rotation support.

12 Claims, 21 Drawing Sheets

(56) References Cited

U.S. PATENT DOCUMENTS

| | | | |
|---|---|---|---|
| 2005/0273025 | A1 | 12/2005 | Houser |
| 2006/0135904 | A1 | 6/2006 | Ingimundarson et al. |
| 2006/0200057 | A1* | 9/2006 | Sterling ................ A61F 5/0123 602/5 |
| 2007/0232975 | A1 | 10/2007 | Castillo et al. |

* cited by examiner

FIG. 10
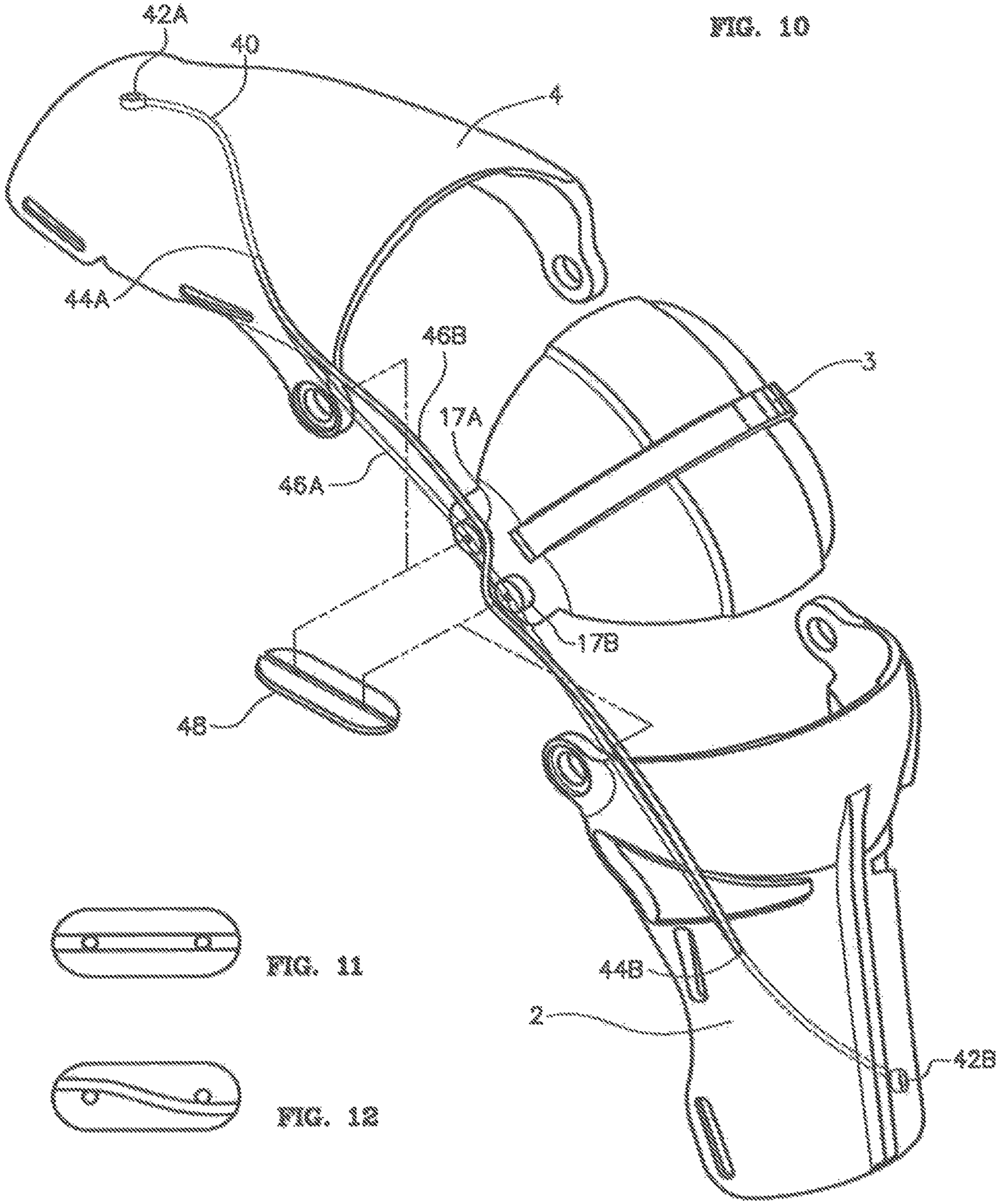
FIG. 11
FIG. 12
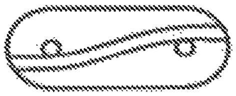
FIG. 13

FIG. 22A-C

CABLE BRACE SYSTEM

INCORPORATION BY REFERENCE

This application incorporates by reference the following: U.S. patent application Ser. Nos. 16/436,786, 13/867,910, 12/987,084, 11/744,213, 62/682,560, and 62/718,529.

PRIORITY CLAIM

This application is a continuation of U.S. patent application Ser. No. 16/436,786 filed Jun. 10, 2019; which is a continuation-in-part of U.S. patent application Ser. No. 13/867,910 filed Apr. 22, 2013; which is a continuation of U.S. patent application Ser. No. 12/987,084 filed Jan. 8, 2011; which is a continuation-in-part of U.S. patent application Ser. No. 11/744,213 filed May 3, 2007. This application also claims priority from U.S. Provisional Application Nos. 62/682,560 filed Jun. 8, 2018, and 62/718,529 filed Aug. 14, 2018.

BACKGROUND OF THE INVENTION

The human body contains numerous complex mechanisms vulnerable to injury. For example, the human knee is a complex mechanism that is highly vulnerable to injury in sports like football, hockey, skiing, snowboarding, and motocross. In these kinds of physically demanding sports the Anterior Cruciate Ligament (ACL) and Medial Collateral Ligaments (MCL) are commonly injured. The wrist, ankle, and elbow are also vulnerable during many of the same activities and for many of the same reasons. The wrist is made up of numerous ligaments which can suffer hyperextension, which is painful and the healing process slow. The ankle and elbow are also at risk to hyperextension events without proper bracing.

Most prior art (conventional) brace devices for ligament protection consist of a rigid plate connected by hinges or straps on either side of the ligament or joint, or are simply two plates connected by straps. The plates are strapped to the leg or arm tightly above and below the ligament/joint with straps that encircle the leg/arm. The current state of the art in functional knee bracing, for example, generally relies on a hinged framework fixated to the knee anatomy by an adjustable strapping system. Although adequate for controlling lower pathology inducing loads, these brace systems have not been shown to be effective at controlling the more clinically important higher loads. As a result, current knee bracing is not fully successful at preventing ligament injury or re-injury. There is a need for a brace design which addresses more specifically the mechanism of ligament injury while maintaining comfort, fit, lightweight design, and unobtrusive sports functionality.

It is the object of the invention to provide a joint and ligament bracing system that bolsters the body's natural ligaments to reduce the proneness to injury or re-injury. This is accomplished, in various embodiments, using a novel control loop strategy, where two or more cables surround separate points near the joint, in order to provide precise control of its movement. These control loops provide a higher level of adjustability, and transfer their tightening force toward the center of the loops, increasing the brace's stability and effectiveness.

One embodiment of the invention is a cable system that acts much like the body's natural Anterior Cruciate Ligament (ACL) and Medial Collateral Ligaments (MCL). The cables are routed around the knee joint in a way that resists the forces that cause excessive joint movement and injury to the ACL and or MCL. As the leg travels through the range of motion, extending a first control loop, the opposite control loop portion of the cables tighten, preventing the tibia bone from moving forward (hyperextending) or twisting (lateral rotation) or bending laterally with respect to the femur.

The cable systems described herein can be tailored or adapted to prior art (conventional) braces increasing their effectiveness.

BRIEF DESCRIPTION OF THE DRAWINGS

FIG. 10 is an exploded isometric view of the individual parts of the secondary cable knee brace system.

FIG. 11 is an inside elevation/side view of the secondary cable guide plate that guides the secondary cable through the pivot points.

FIG. 12 is an inside elevation/side view of an alternate cable guide plate that guides the secondary cable under and over the pivot points.

FIG. 13 is an inside elevation/side view of another alternative cable guide plate that guides the secondary cable over and under the pivot points.

DETAILED DESCRIPTION

Various embodiments to a cable adjusted joint and ligament brace having at least two control loops are described herein. The fundamentals of the present invention can be applied to support various joints and corresponding ligaments, as necessary. In each of the various embodiments, at least two control loops are formed by a cable system, attached to one or more plates or shells near the joint or ligament in need of support.

Knee Brace

Figure 1:
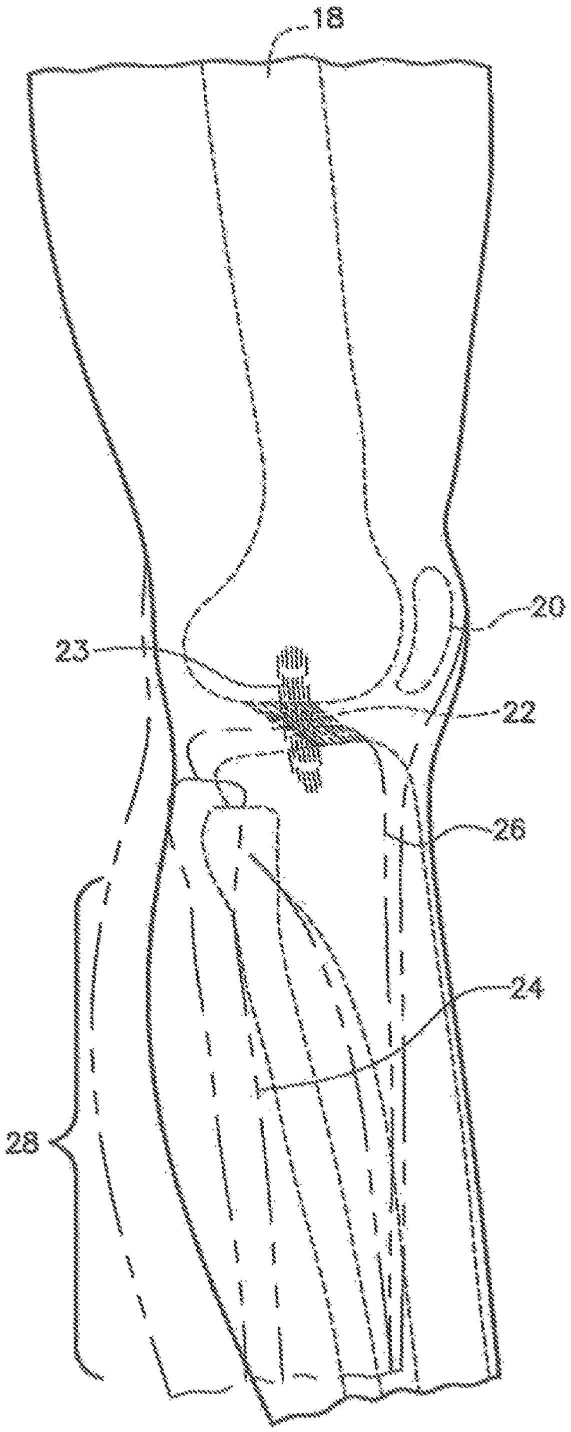
FIG. 1 is an outside elevation/side view of a right leg showing normal fully extended and hyperextended (tearing ACL) views.
Figure 2:
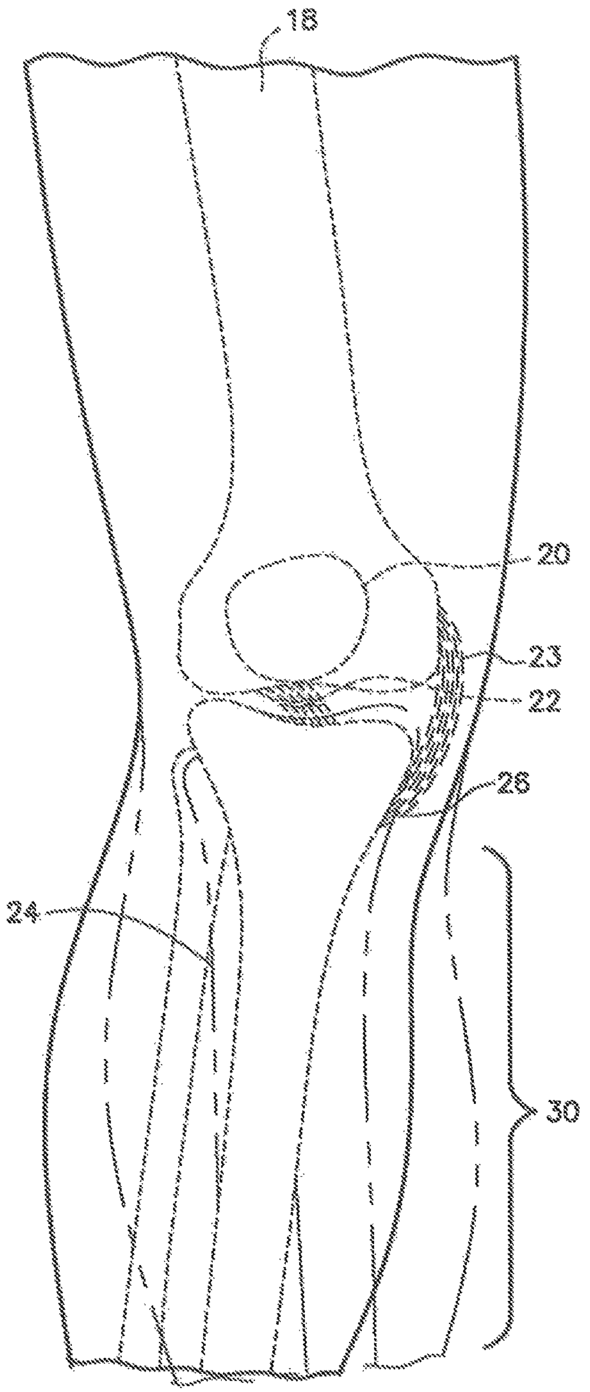
FIG. 2 is a top/front view of the right leg fully extended showing normal and laterally rotated or laterally bent (tearing ACL and or MCL) views.

To be effective in preventing injuries to the ACL 22 and or MCL 23, a knee brace must prevent the tibia bone 26 from moving forward (hyperextending), see FIG. 1, or laterally bending and or rotating (twisting), see FIG. 2, with respect to the femur bone 18. The patella 20 and fibula bone 24 are shown for completeness. The knee brace of this invention as best shown in FIGS. 3-17, which like references refer to like elements throughout the several views, introduces a novel cable system that more effectively prevents hyperextension, lateral bending and or lateral rotation of the knee joint.

Figure 3:
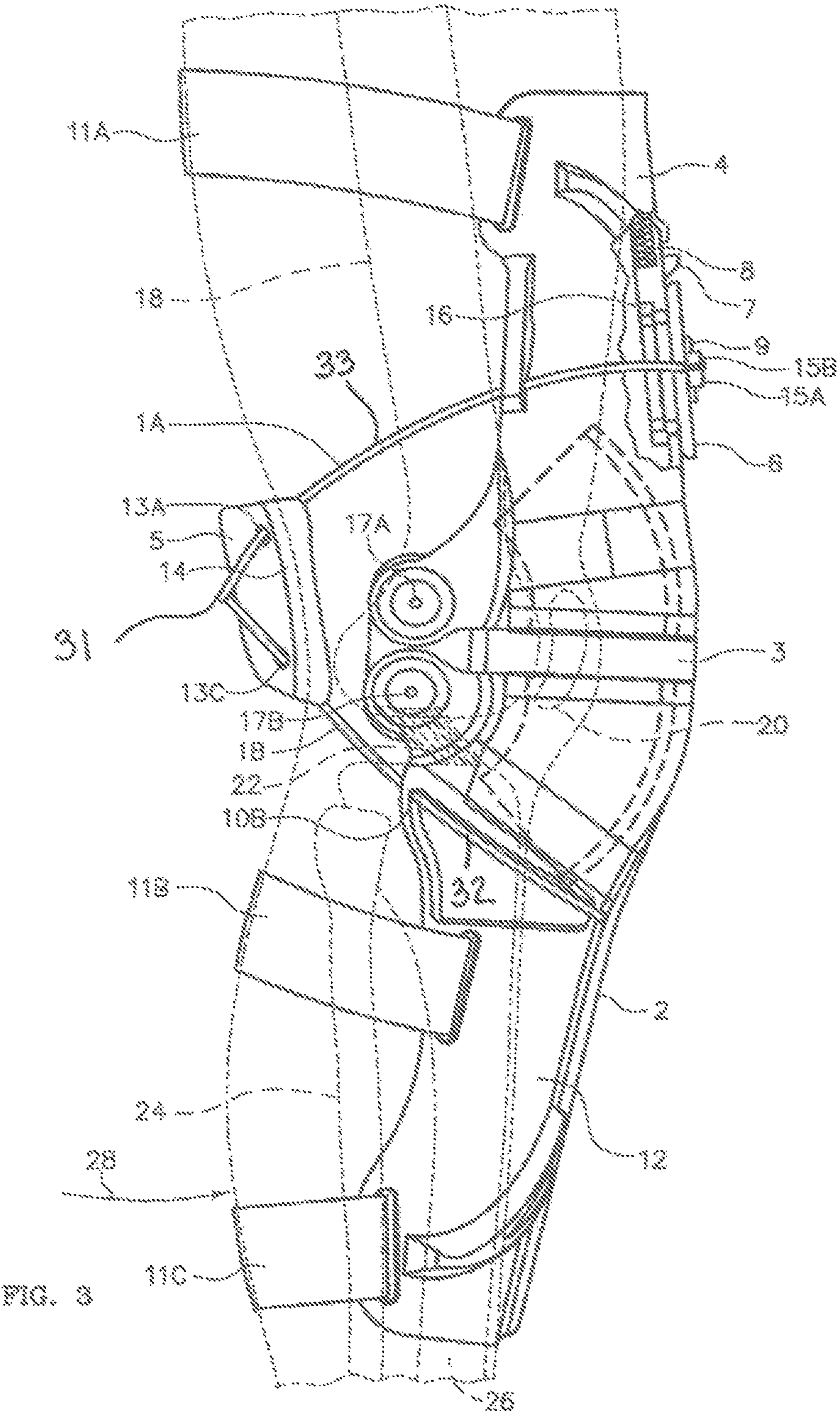
FIG. 3 is an outside elevation/side view of the right leg fully extended showing the primary cable resisting hyperextension of the leg.
Figure 4:
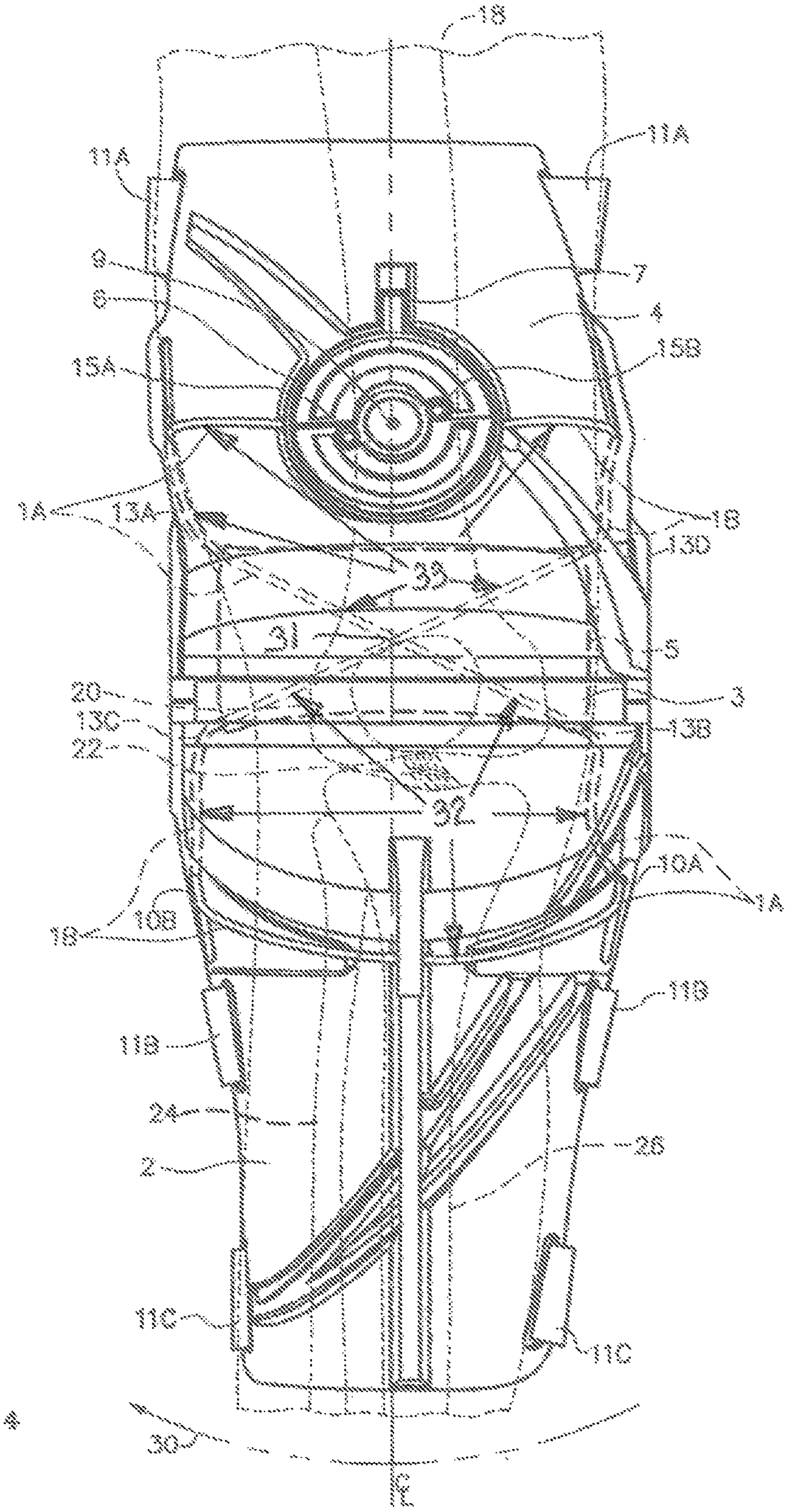
FIG. 4 is a top/front view of the right leg fully extended showing the primary cable resisting lateral rotation of the leg.
Figure 5:
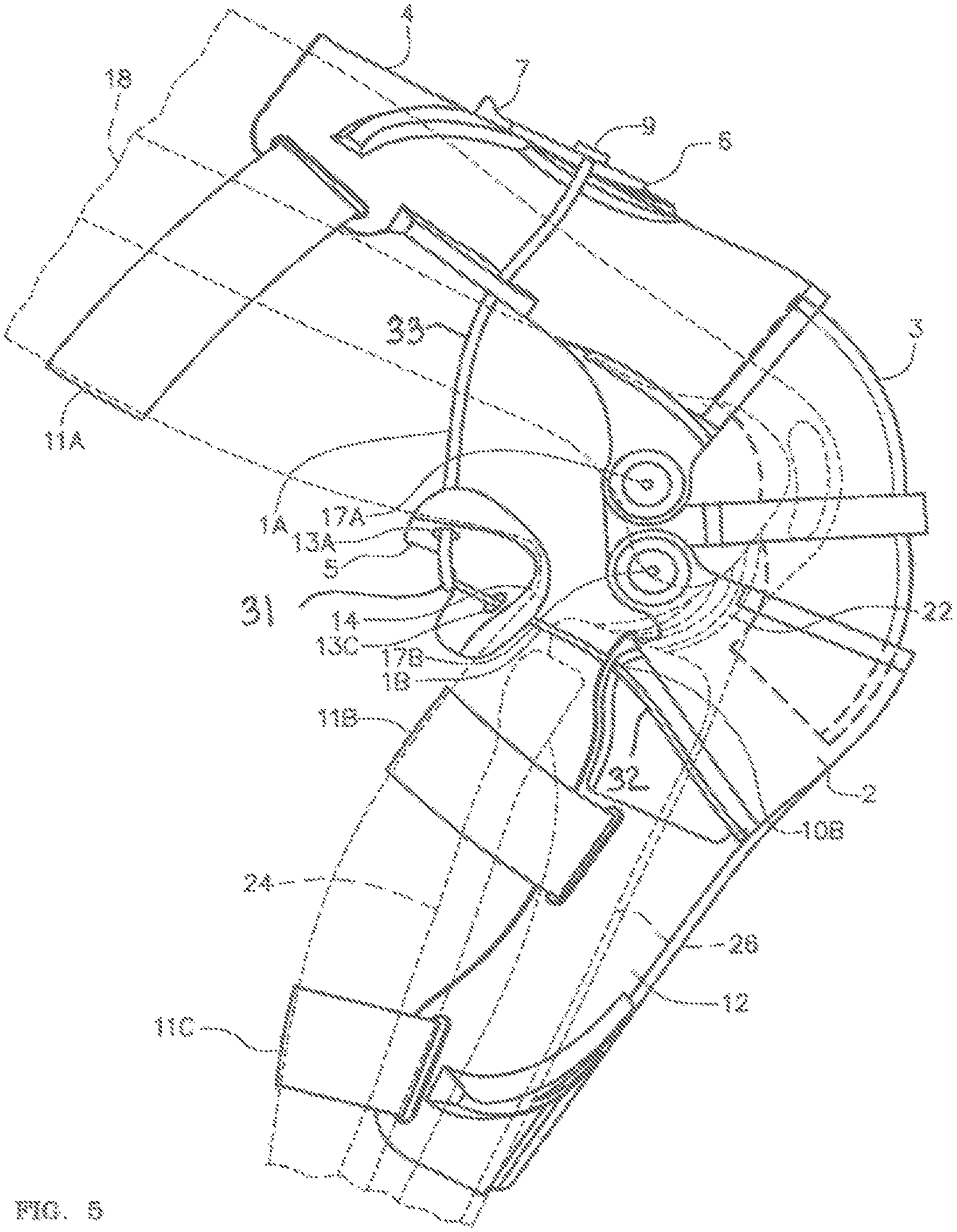
FIG. 5 is an outside elevation/side view of the right leg in the flexed position showing the primary cable knee brace system.
Figure 7:
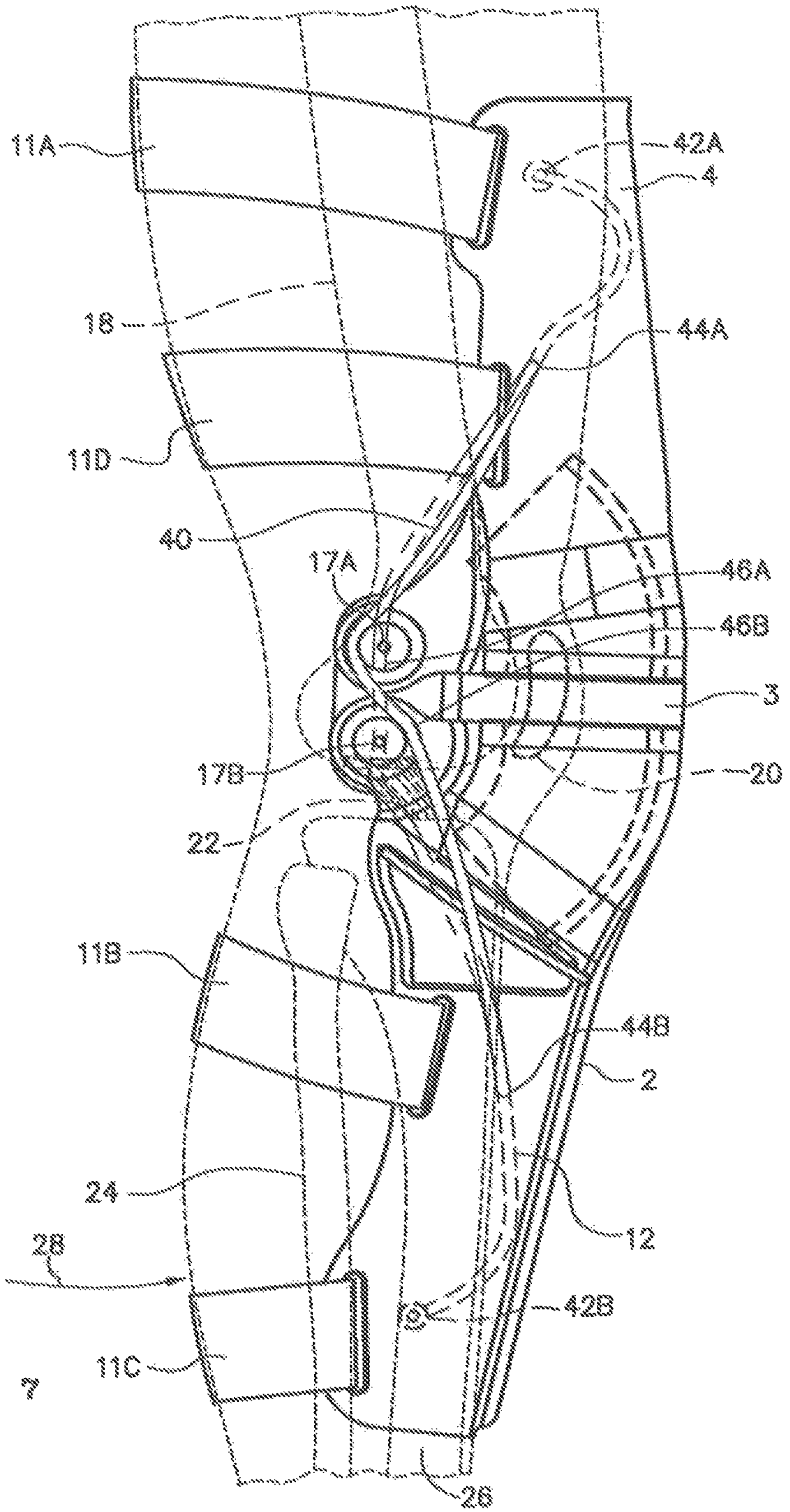
FIG. 7 is an outside elevation/side view of the left leg fully extended showing the secondary cable resisting hyperextension of the leg.
Figure 8:
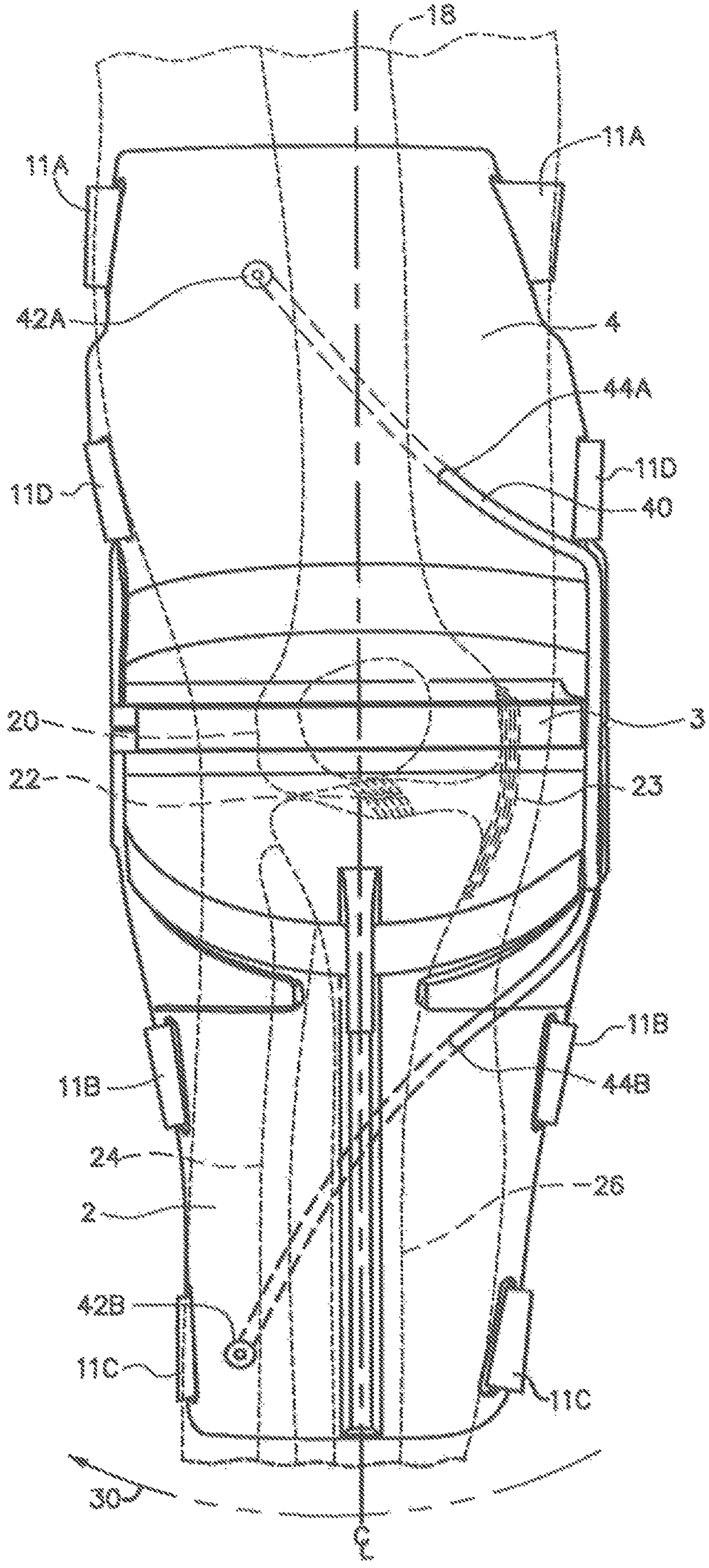
FIG. 8 is a top/front view of the right leg fully extended showing the secondary cable resisting lateral rotation and or lateral bending of the leg.
Figure 9:
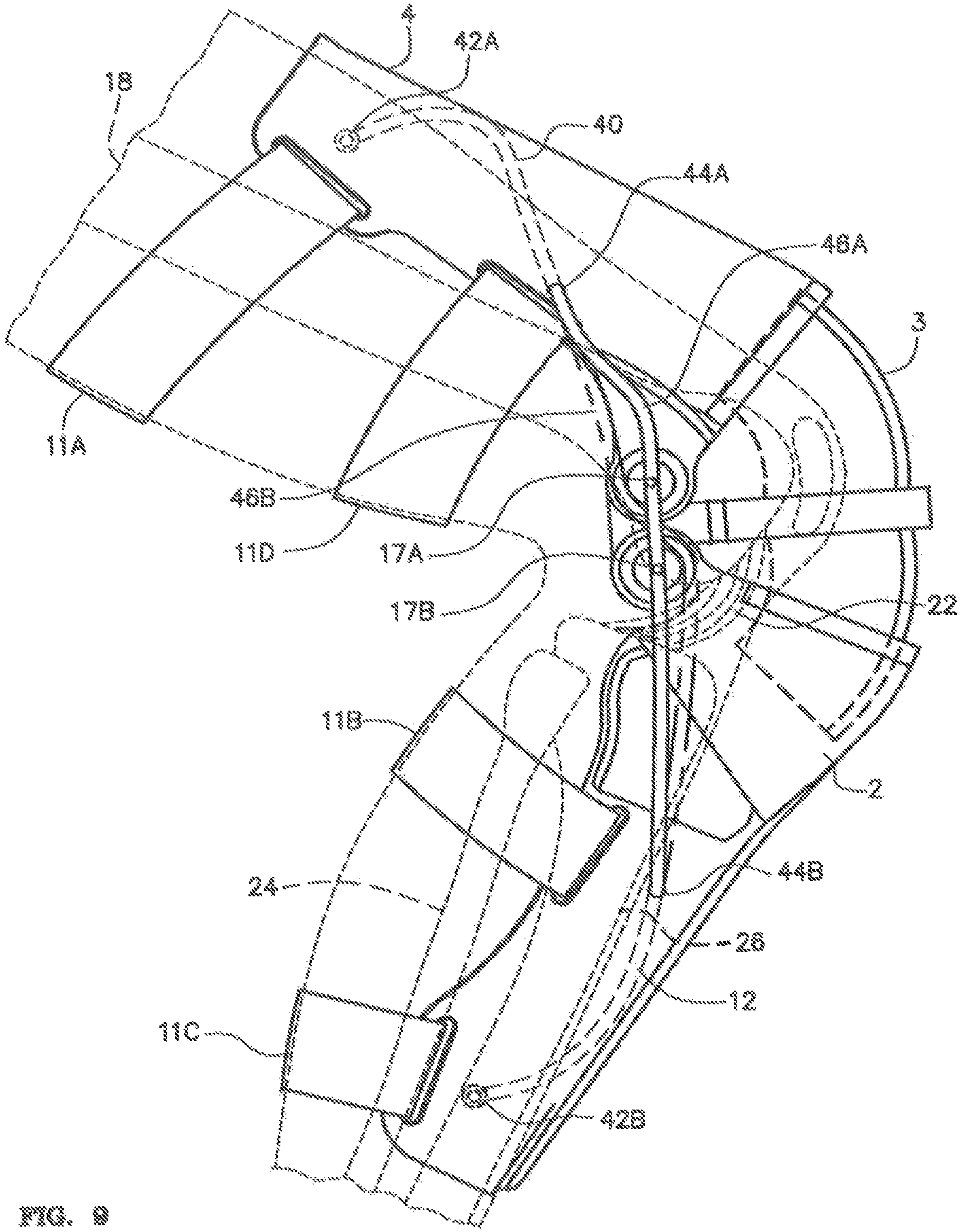
FIG. 9 is an outside elevation/side view of the left leg in the flexed position showing the secondary cable resisting lateral bending or lateral rotation.

FIG. 3 shows the primary cable system of this invention creating an effective differential force to the tibia 26 relative to the femur 18 and reinforcing the ACL 22. When the primary cable 1 of this system is properly tensioned, the brace acts like the body's own ACL 22. Causing it to become taut as the leg extends, resisting the forward movement of the tibia bone 26, with respect to the femur bone 18. FIG. 4 shows the primary cable system of this invention resisting the lateral rotation of the tibia bone 26, with respect to the femur bone 18. FIG. 5 shows the primary cable system of this invention when the leg is flexed. Because the tibial plate 2 moves further away from the femoral plate 4 as the leg extends the primary cable 1 becomes progressively tighter as the leg approaches full extension, as shown in FIG. 3. When a hyperextension force 28 is applied to the leg, as shown in FIG. 3, the tibial plate 2, patellar plate 3, and femoral plate 4 are compressed together as the primary cable 1 comes under progressively more tension. The tensile force in the primary cable 1 pulls down on the tibial plate 2, and up on the back plate 5 creating the differential resistive force across the knee joint preventing hyperextension of the leg. FIG. 7 shows the secondary cable system of this invention creating an effective differential force to the tibia 26 relative to the femur 18 and reinforcing the ACL 22 and MCL 23. As the leg extends the secondary cable 40 resists the forward movement of the tibia bone 26, with respect to the femur bone 18. FIG. 8, shows the secondary cable 40 resisting the lateral bending and/or lateral rotation of the tibia bone 26, with respect to the femur bone 18. FIG. 9 shows the secondary cable system of the invention when the leg is flexed and the secondary cable 40 resisting lateral bending and lateral rotation throughout the legs range of motion. As the leg extends the patellar plate 3 acts like a hinge for the tibial plate 2 and femoral plate 4 rotating about pivot points 17*a* and 17*b*, respectively, approximating the knees flexion-extension movement.

When a lateral rotation force 30 is applied to the leg, as shown in FIG. 4, the tibial plate 2, patellar plate 3, femoral plate 4, and back plate 5 are held rigid by the tension developed in the primary cable 1. The tensile forces in primary cable 1 cross behind the leg, creating cable cross over point 31, as they pass through back plate 5 resisting rotation and bending across the knee joint preventing the leg from laterally bending or rotating. When a lateral bending or lateral rotation force is applied to the leg as shown in FIG. 8 the tibial plate 2, patellar plate 3, and femoral plate 4 are held rigid by the tension developed in the secondary cable 40. The tension in the secondary cable 40 prevents the brace from bending across the knee joint preventing the leg from laterally bending or rotating.

This invention comprises of a primary cable 1 and secondary cable 40 that can be made of any flexible material with a sufficiently high tensile strength. A tibial plate 2 that could be made of any rigid or semi rigid material is shaped to conform to the tibia bone 26, beginning just below the knee and ending approximately at the midpoint of the tibia bone 26. The tibial plate 2 is held in position with straps 11*b* and 11*c*. Foam padding 12 is attached to the underside of the tibial plate 2 for comfort and to provide a firm grip on the individual's tibia bone 26. A patellar plate 3 that could be made of any rigid or semi rigid material connecting the tibial plate 2 to the femoral plate 4. A femoral plate 4 that could be made of any rigid or semi rigid material is located on top of the thigh from just above the knee to approximately mid femur 18 and is held in position with strap 11*a*. Back plate 5 could be made of any rigid or semi rigid material and is located behind the leg just above the knee joint, keeping cable 1 in the proper location and firmly holding the femur bone 18 as the differential force of the primary cable 1 is transmitted across the joint. Foam padding 14 is attached to the inside of the back plate 5 to help spread the force of the primary cable 1 comfortably to the leg. A cable tensioner dial 6 and locking/release button 7 with spring 8 are attached to the femoral plate 4 with retainer screw 9. These could be made from any metal or rigid material that will withstand the forces required to keep the primary cable 1 locked in place during use. Other cable tensioning and locking mechanisms could be used, but the dial tensioning and locking system gives a very wide range of fine tuned cable adjustability and ease of use.

Figure 6:
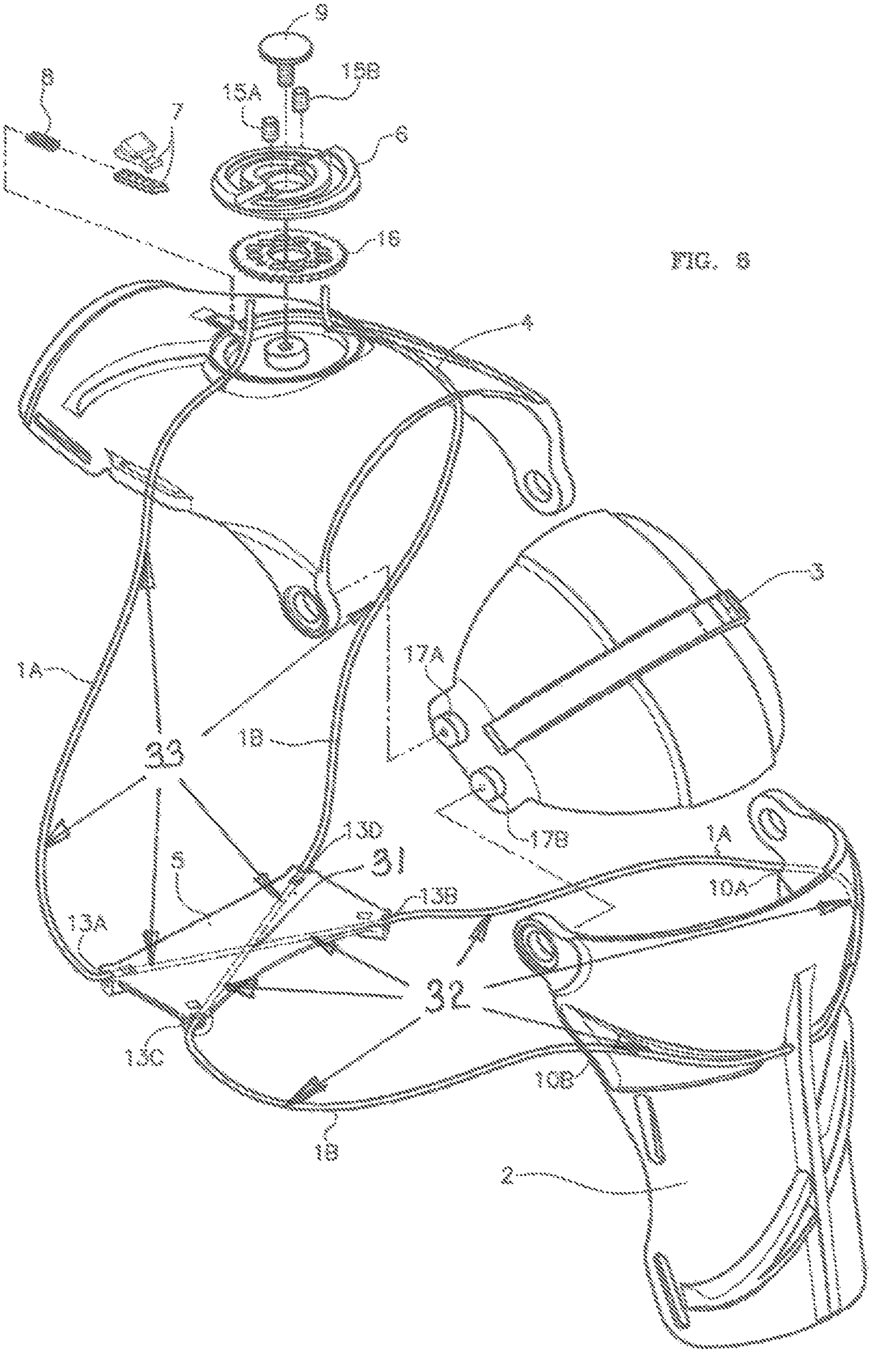
FIG. 6 is an exploded isometric view showing the individual parts of the primary cable knee brace system.

The fundamental element of this invention is the routing of the cables. As best shown in FIG. 6, primary cable 1 begins attached to femoral plate 4 by cable connector 15*a*, crosses behind the leg through cable guide hole 13*a* and cable guide hole 13*b* in back plate 5 and runs through a cable guide hole on the opposite side of tibial plate 2. The primary cable 1 then loops over the leg through a cable guide hole and through the cable guide hole to the other side of tibial plate 2. From the cable guide hole in tibial plate 2, the primary cable 1 again crosses behind the leg through cable guide hole 13*c*, crossing over itself, creating cable cross over point 31, before going through cable guide hole 13*d* in back plate 5, and attaches to the opposite side of femoral plate 4 by second cable connector 15*b*.

In additional embodiments, primary cable 1 begins attached to femoral plate 4 by first cable connector 15*a*, crosses behind the leg through first cable guide hole 13*a* and second cable guide hole 13*b* in back plate 5, and attaches to the opposite side of tibial plate 2 with clamping screw 10*a*. The primary cable 1 then loops over the leg attaching to the other side of tibial plate 2 with clamping screw 10*b*. From clamping screw 10*b* the primary cable 1 again crosses behind the leg through third cable guide hole 13*c* and fourth cable guide hole 13*d* in back plate 5, creating cable cross over point 31, and attaches to the opposite side of femoral plate 4 by second cable connector 15*b*.

As best shown in FIG. 10, secondary cable 40 begins attached to the outside, or lateral side, of the femoral plate 4 by the femoral cable connector 42*a* and runs through the femoral cable guide hole 44*a*. The secondary cable 40 crosses femoral pivot point 17*a* and tibial pivot point 17*b* through cable guide plate 48. From there, the secondary cable 40 runs through tibial plate guide hole 44*b* and attaches to the outside, or lateral side, of the tibial plate 2 by the tibial cable connector 42*b*, completing the route.

In some embodiments, a single cable is used as it passes through the various guides. In alternative embodiments, the cable could be made up of individual segments connected together to form the completed routing. For example, first primary cable segment 1*a* and second primary cable segment 1*b* can be connected together with tibial plate 2 to complete the loop. First primary cable segment 1*a* begins attached to femoral plate 4 by first cable connector 15*a*, crosses behind the leg through the cable guide hole 13*a* and cable guide hole 13*b* in back plate 5 and attaches to the opposite side of tibial plate 2 with clamping screw 10*a*. Without having to loop over the leg, the second primary cable segment 1*b* is attached to the opposite side of tibial plate 2 with clamping screw 10*b*. From clamping screw 10*b*, the second primary cable segment 1*b* crosses behind the leg through the cable guide hole 13*c*, and crossing over itself, creating cable cross over point 31, before going through cable guide hole 13*d* in back plate 5 and completes the loop by attaching to the opposite side of femoral plate 4 with cable connector 15*b*.

The segments of the cable extending from the cable cross over point 31 to the tibial plate portion of the brace and returning to the cable cross over point 31 form the tibial control loop portion 32 of the cable. The segments of cable extending from the cable cross over point 31 to the femoral plate portion of the brace and returning to the cable cross over point 31 forming the femoral control loop portion 33 of the cable. FIG. 6, for example, illustrates these control loop portions 32 and 33. During use, for example when the knee is extended toward hyperextension, the tibial control loop will lengthen, causing an inverse tightening of the femoral control loop.

The primary cable 1 is adjusted by turning the cable tensioner dial 6 taking up the excess primary cable 1 length. The primary cable 1 is automatically locked into place by the ratcheting gears 16 on the cable tensioning dial 6 and spring 8 actuated locking/release button 7. The button 7 is also used to release the tension in primary cable 1 for installation and removal of the brace.

While an infinite number of secondary cable routings across the pivot points are possible, directly through the pivot points as shown in FIG. 9, 46*a* is most desirable to achieve optimum tension on the secondary cable 40 throughout the leg's full range of motion. FIG. 11 shows a cable guide plate which guides the cable directly through the pivot points, secondary cable routing 46*a*, as described above. Alternate secondary cable guide plate configurations, as shown in FIGS. 12 and 13, could be used guide the secondary cable around the pivot points. For example, alternate secondary cable routing 46*b* could be achieved using the cable guide plate, as shown in FIG. 13, which guides the secondary cable 40 over, or to the fore of, femoral pivot point 17*a* and under, or to the aft of, tibial pivot point 17*b*.

Figure 14:
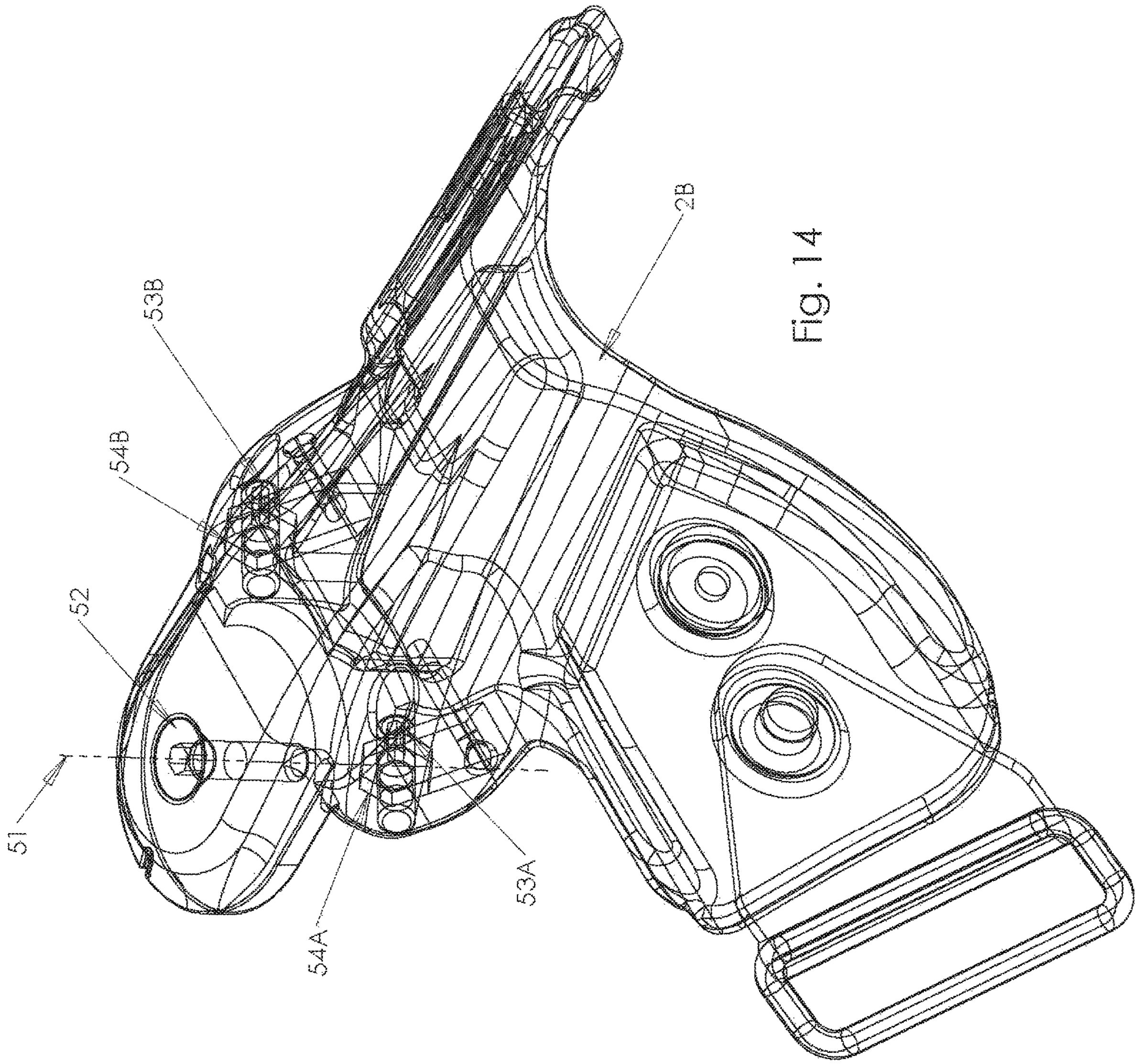
FIG. 14 is a top view of a portion of a Q-adjustable tibial shell according to an embodiment of the present invention.
Figure 15:
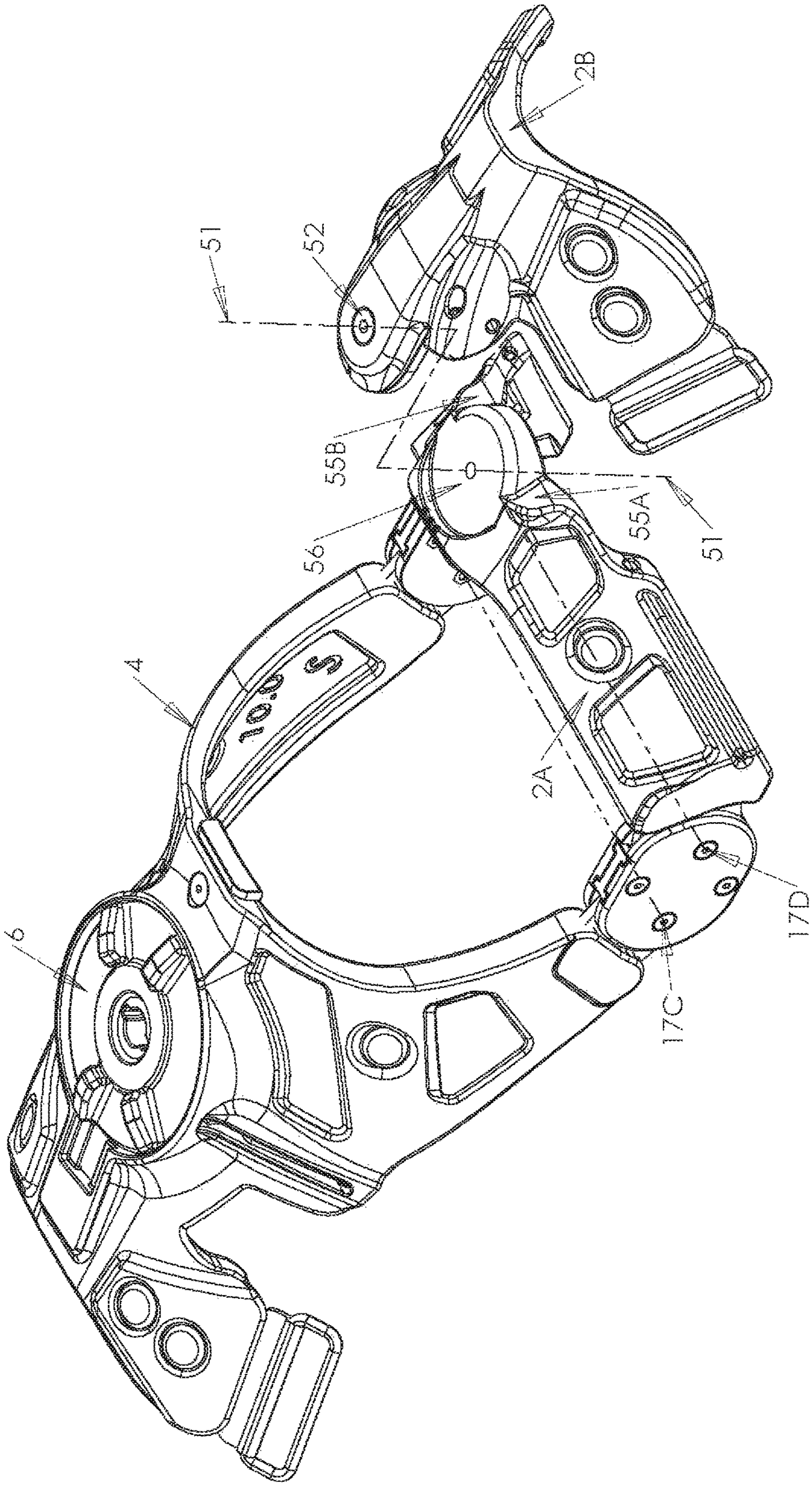
FIG. 15 is a three-quarter view of a Q-adjustable leg brace according to an embodiment of the present invention.
Figure 16:
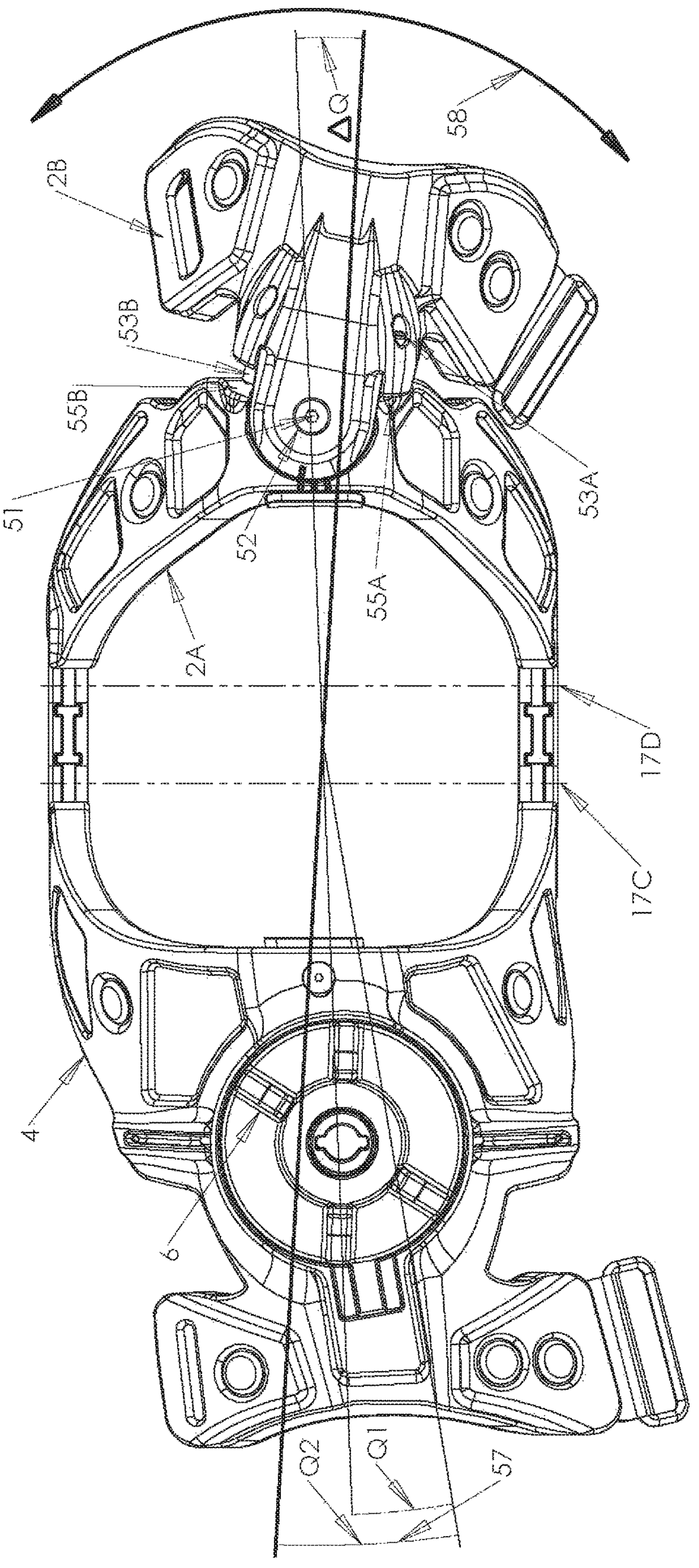
FIG. 16 is a top down view of a Q-adjustable leg brace according to an embodiment of the present invention.

FIG. 15 depicts an alternative tibial shell arrangement. When configured in this manner, the tibial shell 2B mounts to the tibial shell 2A at point 51, forming the axis of rotation. The shell 2B is secured to the tibial shell 2A using tibial adjustment locking screw 52. The tibial shell 2B rotates about axis 51 in order to establish the desired Q-angle, as depicted in FIG. 16. The relative rotation of the tibial shell 2B about axis 51 is controlled using screws 53A-B on either side of the tibial shell 2B as depicted in FIG. 14. By lengthening or shortening the adjustment screws, which push against corresponding bearing surfaces 55A-B, the tibial shell pivots accordingly about the axis 51.

FIG. 14 best depicts the adjustment mechanism showing adjustment screws 53A-B threaded through retention nuts 54A-B in tibial shell 2B. As best shown in FIG. 16, after loosening adjustment locking screw 52 and then shortening adjustment screw 53A, lengthening adjustment screw 53B pushes against bearing surface 55B on tibial shell 2A, forcing tibial shell 2B to rotate clockwise about axis 51 until adjustment screw 53A contacts bearing surface 55A on tibial shell 2A before tightening adjustment locking screw 52.

Cable guides accept the cable, the cable being comprised of one or more segments, which transfers energy to control knee movement and prevent hyperextension of the knee joint in the same manner as the other embodiments described above, for example, FIGS. 2-6. In the same manner as the embodiments described above, the cable may be composed of one or multiple portions. While the routing of the cable is not depicted, in a preferred embodiment, the cable beginning from cross over point 31, extends to a first side of tibial shell 2A passing through one or more cable guide holes, then extends over tibial shell 2B through one or more cable guide holes, and then extends back down the opposite side of tibial shell 2A through one or more cable guide holes and then extends back to cable cross over point 31, forming the tibial control loop 32

When the knee of the user extends, the cable portion extending from a cross over point 31 around the tibial shell 2B and returning to the cross over point, the tibial control loop 32 lengthens accordingly. This produces a direct response in the portion of the cable which extends from the cross over point 31 over and around the femoral plate, the femoral control loop. That portion of the cable tightens, bringing the femoral plate and the backplate into the leg and behind the knee joint respectively, and stopping further extension of the knee by controlling the length of the tibial control loop.

FIG. 15. Depicts both the femoral shell 4 and tibial shells 2A and 2B of a knee brace according to an embodiment of the present invention. Notably, the back plate, straps, and cable routing are absent in order to more clearly depict the arrangement of the adjustable tibial shell 2B. As depicted, the invention according to this alternative embodiment maintains many of the features described in alternative embodiments herein, including: 4, 6, 17C and 17D. FIG. 15 depicts the tibial shell 2B of FIG. 14 as well as its mounting surface 56 on tibial shell 2A. The axis of rotation 51 is clearly depicted as running through the point at which the tibial shells 2A-B are connected.

Foam padding may be strategically placed at various points on the inside portions of the brace depicted in FIG. 15. For example, on the sides near hinge point 17C and 17D, and underneath tibial shells 2A and 2B as well as femoral shell 4. This foam provides increased comfort to the user.

FIG. 16 depicts the adjustability of the tibial shell 2B which creates a chosen Q-angle 57. The angle between the tibia and the femur forms the quadriceps angle, herein referred to as the Q-angle 57. This angle varies depending on the physiology of the user. The tibial shell 2B is adjustable in order to customize the Q-angle 57 to accommodate each user. By turning the adjustment screws 53A-B, the Q-angle 57 may be changed as the tibial shell 2B pivots 58. The Q-angle is adjustable in either direction. In preferred embodiments, the Q-angle 57 is adjustable up to 4 degrees in either direction, ΔQ. A Q-angle of less than average is defined as *Varus*. In this embodiment, the Q-angle 57 may be referred to as negative, for example, the brace may be adjusted −4 degrees from average, ΔQ, forming a more acute Q-angle 57. A Q-angle greater than normal is referred to as Valgus, and may be formed by adjusting the brace to increase the Q-angle, for example +4 degrees from average. The depicted arrangement in FIG. 16 shows, for example, a Valgus arrangement, where the Q-angle of the brace, Q2, is greater than an average angle, Q1. In order to achieve this, the tibial plate 2B has been adjusted toward the outside of the user's leg (right side knee brace). Once the user is happy with their customized Q-angle, they can lock the brace using locking screw 52. This prevents the Q-angle from changing while the user is wearing the device.

Figure 17:
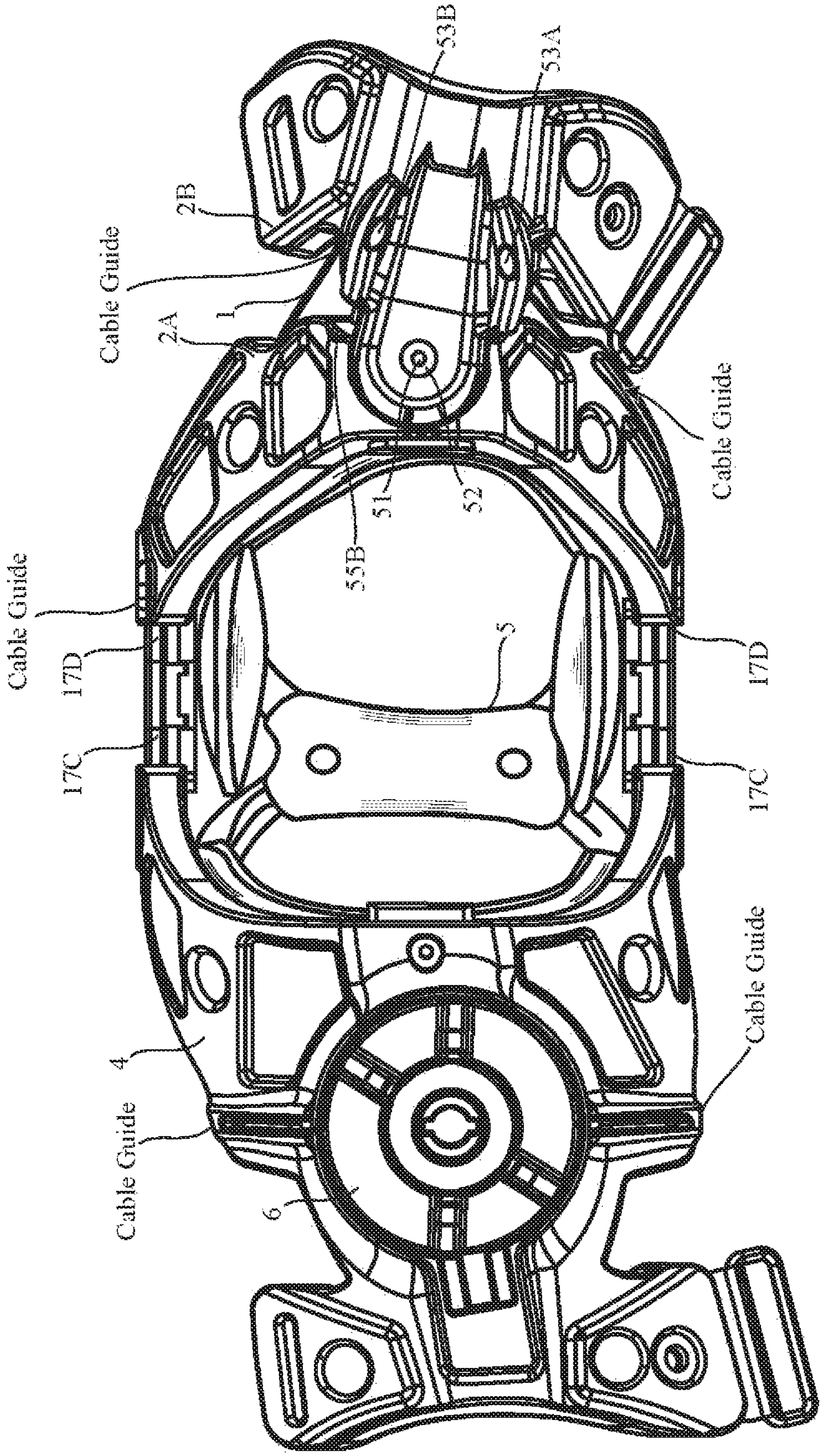
FIG. 17 is a top down view of a Q-adjustable leg brace according to an embodiment of the present invention.

FIG. 17 depicts an embodiment of the present invention with the femoral back plate 5 installed. As depicted, the back plate is positioned just above the knee joint, behind the user's knee. The back plate 5 guides the portions of the cable 1 to a cross over point 31, not shown, located on its back side. Each portion of the cable 1 is then guided back up toward the upper portion of the brace, for example to either side of the femoral plate 4, and the first tibial plate 2A. Cable guide holes along the perimeter of tibial plate 2A are also shown, these guide holes receive the cable from the femoral back plate 5, and guide the cable 1 along tibial plate 2A toward and to tibial plate 2B where the cable 1 enters another guide hole in tibial plate 2B before crossing over to the other side of tibial plate 2B and returning along the same path on the opposite side of the brace. This portion of the cable's path, from the cross over point 31 to the tibial plate 2B and back forming the tibial control loop 32. A similar path occurs where the cable 1 extends from the cross over point 31 on the femoral back plate 5 up to cable guides on either side of the femoral plate 4, connecting to the adjustment mechanism 6.

In additional embodiments of the present invention, the tibial plate may include additional portions which increase the hold on the wearer's tibia. Increased tibia control offer additional protection from hyperextension. As there is little tissue between the tibia and the external portion of the leg, this area is ideal for control of the leg. In some embodiments, the underside of the tibia plate, closest to the user's leg, may include an additional semi-ridged portion. As the cable system is tightened, for example, this semi-ridged portion conforms to the shape of the user's tibia. This provides an increased hold on the tibia.

In additional embodiments of the present invention, the tibial plate may include additional portions which increase the hold on the wearer's tibia. Increased tibia control offer additional protection from hyperextension. As there is little tissue between the tibia and the external portion of the leg, this area is ideal for control of the leg. In some embodiments, the underside of the tibia plate, closest to the user's leg, may include an additional semi-ridged portion. As the cable system is tightened, for example, this semi-ridged portion conforms to the shape of the user's tibia. This provides an increased hold on the tibia.

In additional embodiments of the present invention, the tibia plate may be constructed such that the plate has varying flexibility across itself. For example, this varying flexibility would allow the tibia plate to conform to the shape of the user's leg, while also providing the necessary rigidity. In this example, a second semi-ridged portion may not be required, or, alternatively, may be offered in addition to the second semi-ridged portion.

In additional embodiments of the present invention, the user may, of course, use the brace as a preventative device, before any damage occurs, as opposed to after. In such a case, additional protection may be required. For example, user's engaged in extreme sports may require supplemental protection from impacts. Embodiments of the present invention may, therefore, include knee caps which protect the knee from strike forces. In some embodiments, the knee cap portion is disposed between the tibial and femoral plates such that when the plates pivot away from one another, the knee cap remains in place. In such an example, the tibial and femoral plates glide over or beneath the knee cap portion so as to allow necessary flexibility. Further, additional padding at the front of the knee may be added in order to both support the knee and protect it from strike forces.

When forces are applied to the knee joint the cable becomes tight and resists the excessive movement that can cause injury to the ligaments. As the cable tightens it squeezes the Brace Shells gripping the tibia and femur. The Tibial Shell is designed to grip the Tibial Tuberosity controlling the lower leg, while simultaneously the Femoral Shell and Tendon Back Plate grip the femur. The patellar cup being incorporated into the hinge mechanism provides enhanced structural rigidity which provides better protection against collateral ligament injury. Additionally, the PCL is protected from the common mechanism of a direct blow to the anterior proximal tibia on a flexed knee because the tibial plate is rigidly fixed to the patellar cup in turn well fixated to the distal femur and thus resisting a posterior translatory force to the tibia.

Changes and modifications can readily be made to adapt the tibial shell Q angle adjustment invention to conventional knee braces. It is also anticipated that this invention can be adapted to an elbow brace by substituting the adjustable tibial shell with an adjustable radius shell. This allows a symmetrical elbow brace to be adjusted to fit the angle between the humerus and radius of the user's arm, and can be adjusted to fit a right or left arm.

Wrist Brace

An additional embodiment of the present invention is a cable system for a wrist brace. The cable system supports the wrist and does not cause arm pump. The cable system provides a progressive flexion support of the wrist, while also being low profile and smaller in footprint than traditional braces.

Another embodiment of the present invention provides a user with a wrist brace using one or more cables in order to provide progressive support through flexion of the wrist such that increased wrist movement is met with increased support. Such an embodiment enables easy adjustability of extension, and also provides increased support to the wrist ligaments. Many of the components discussed above are common to the wrist brace embodiment.

Conventional braces are limited in their effectiveness resisting excessive joint movement that causes injury to the wrist. Even when the strapping devices are tightened to the point of discomfort, they have limited effect preventing excessive movement of the wrist joint. Prior art braces also fail to provide support throughout the range of movement, progressive support.

Additionally, prior art wrist braces often require expensive customization, such as sending gloves to a manufacture to have pieces sewn on. Due to the way traditional braces mount to the user's arm, and the level of tightness required, wearers often complain of "arm pump."

Further still, traditional braces do not allow a user to continue using their hand, or offer extremely limited use. For this reason, user's heavily dislike wearing the brace, and the brace cannot practically be worn as a preventative measure during many activities.

A wrist supporting device consistent with the disclosures herein may be used both after an injury, as well as to prevent injury. This is unique, since the present invention allows the user to retain use of his/her hand.

Preferably, the wrist brace is low profile and conforms to the user's lower arm and wrist area. One or more plates are positioned on the upper portion of the user's arm and hand. A second, smaller plate is positioned toward the underside of the user's hand and arm. A cable runs between these plates. The guide plates themselves include small openings to receive the cable to control its path. The cable can be tightened using an adjustment mechanism consistent with the disclosure herein. The cable may also provide progressive resistance, which may be adjustable, while also providing a stopping point, past which movement of the wrist will be prevented or restricted. Progressive resistance is provided such that as the user bends his or her wrist, additional tension is placed on the wrist, preventing hyperextension.

In various embodiments, the upper plates consist of a metacarpal shell and a radius shell, which may together for a single or separate shells, and the lower plate consists of one or more tendon back plates.

Various embodiments may include multiple smaller metacarpal and radius shells, and multiple tendon back plates. For example, in such an embodiment employing separate metacarpal and radius shells and one or more tendon backplates, there may also be two cables.

The cable, or cables may form two or more loops, where the more forward (toward the user's hand) of the upper and lower guide plates are connected (metacarpal control loop), and the more rearward (toward the upper arm) are connected (radius control loop). In embodiments with one cable, the cable may not be fully connected, such that the cable can include two discrete distal ends.

In various additional embodiments, the metacarpal and radius shells or tendon back plate may be shaped in order to accomplish additional goals. For example, if upward movement of the wrist is necessary, the radius shell may not extend as far into the back of the user's hand. Additionally, the tendon back plate may be shaped to conform to the underside of the wrist near the palm. Or, alternatively, the tendon back plate may be placed further back, depending on the use case and the activity, for example, if the user desires to retain some movement of the wrist up and down, but prevent twisting or lateral movement. In alternative embodiments, the tendon back plate may be shaped in an X-like pattern, beginning near the palm and extending back, with the legs of the X moving toward the metacarpal and radius shells respectively. These legs may provide guides for the cable(s) (e.g., a tendon back plate cable guide).

The metacarpal or radius shells may also include portions which extend downward, toward the tendon back plate to receive and guide the cable. Either the metacarpal or the radius shells portions also, in many embodiments, will include an adjustment mechanism consistent with the description and teachings herein that allows finite adjustment of the length of the cable. One or more straps may also be included, for example on the forearm, via hook and loop fabric extending from the radius shell, forming a loop around the forearm.

The metacarpal and radius shells may also include one or more hinges. For example, the radius shell may attach to the metacarpal shell by a hinge located near the pivot of the wrist. This may allow control over the wrist in the upward and downward directions. In some aspects, the pivot may include a hinge or other similar mechanism that can be adjusted, in degree, in resistance, or both. In additional embodiments, the hinge may be locked or non-existent. In addition to hinges, the metacarpal and radius shells may also include provisions for one or more straps. For example, the radius shell may include reliefs to allow a strap to wrap around the underside of the user's arm. These straps may help position the brace on the arm, and prevent the brace from moving or sliding on the arm during use.

In additional embodiments, the metacarpal, radius, and tendon back plate shells may be connected to a softer material that makes contact with the user's arm. This softer material may extend beyond the area covered by the upper or lower plates. For example, in some embodiments, the radius shell includes this softer material on its underside, between the shell and the users arm, and further, in some embodiments, this softer material may extend as a portion of material over one or more of the user's fingers in order to provide increased stability to the device. The routing of the cable preferably provides secure, comfortable attachment to the user while also providing progressive support to the wrist.

The cable, as in the knee brace embodiment, can be made of any flexible material with a sufficiently high tensile strength. The upper and lower plates may be made of any rigid or semi rigid material and shaped to conform to the intended area, such as the top of the lower arm extending to the hand, and the underside of the lower arm and palm.

The cable system, along with the shells, provides for progressive support though extension as well as an adjustable extension stop. This support through the range of motion may substantially prevent wrist injuries and hyperextension.

The wrist supporting device is a lower cost alternative to manufacture, being relatively simple in its design. It is also low profile, allowing users to wear the brace proactively in order to prevent injury.

Various additional attachment mechanisms may be employed. For example, as depicted, a strap may be included. In various embodiments, the strap may be included toward the back of the brace and toward the upper arm. In other embodiments, the strap may be more forward.

The cable system of the present invention can extend from an upper plate (e.g. radius shell), through a plurality of guides, and across to a bottom plate, or tendon back plate, back up to the optionally hinged portion, the metacarpal shell, and around and back finishing on the opposite side of the radius shell at the adjustment mechanism housing. When a lateral rotation force is applied to the wrist, the radius shell, separate or integrated metacarpal shell (optionally hinged) and the tendon back plate are held rigid by the tension developed in the cable. The tensile forces in primary cable cross behind the wrist as they pass through tendon back plate resisting rotation and bending across the wrist joint preventing the wrist from laterally bending or rotating. This force is exerted from all points along each of the control loops created at either side of the cross over point, the force applied toward the center of the loop. The tension in the cable prevents the brace from bending across the wrist joint preventing the wrist from laterally bending or rotating.

The tendon back plate provides progressive support to the tendons in the wrist throughout the movement of the wrist. For example, as the users hand bends upwards, the rear control loop (radius) portion of the cable tightens which draws the tendon back plate toward the radius plate and metacarpal plate. This provides additional support to the wrist by unloading the tendons, and also prevents the forward control loop (metacarpal) from continuing to extend. The further the user's wrist bends, the more support is provides as the tendon back plate is drawn into the tendon area.

Figure 18:
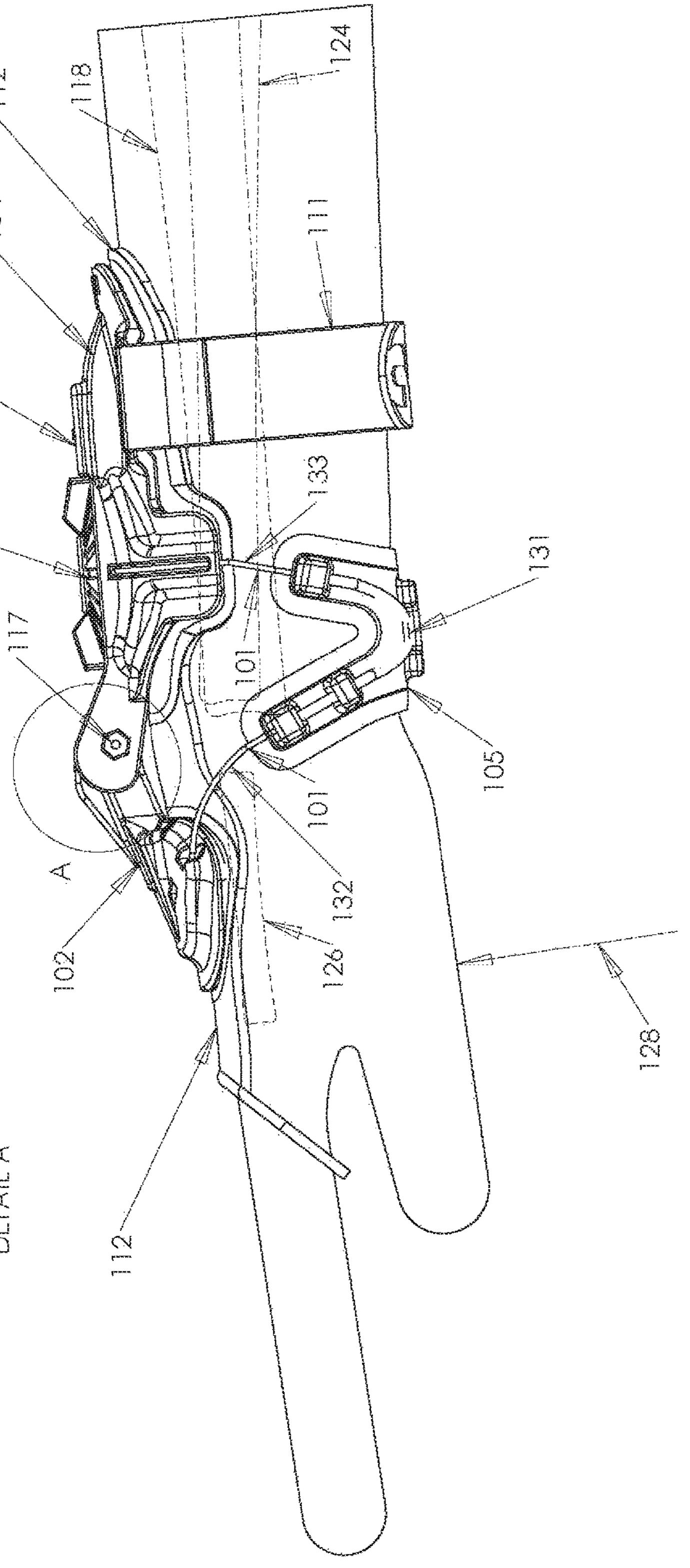
FIG. 18 is an inside elevation/side view of a wrist brace shown on a right wrist consistent with the embodiment of the present invention.

As depicted at FIG. 18, a brace is shown which can stabilize a user's wrist, preventing hyperextension. As depicted, a wrist brace is comprised of semi rigid shells, preferably a radius 104, metacarpal 102, and tendon back plate 105. The shells are preferably constructed of a resilient material and shaped to ergonomically form to the user's wrist. In some embodiments, the material may be moldable to the user, for example, by heating. The shells may take on any number of shapes to accommodate various design changes. For example, as depicted, the radius plate 104 may include small ears (e.g., a radius plate cable guide) which extend downward to guide the cable 101 toward the lower portion. These ears may be moved forward or rearward to change the point of restriction. In some embodiments, the ears may be movable, such that they can be adjusted, while in other embodiments they may be permanent, fixed, and/or rigid.

An adjustment mechanism 106 can be located on the radius shell 104, or optionally on any other shell. The adjustment mechanism dial 106 and ratchet 107 allows for tightening of a cable system. The cable 101 engages the metacarpal shell 102, radius shell 104, and tendon back plate 105, and when tightened, brings the shells toward one another.

The cable system also provides progressive support, such that, as the user's wrist is subjected to a hyperextension force 128, increased extension is met with increased restriction. Two control loops are also formed by the cable portions. The metacarpal control loop 132 is formed by the portion of the cable extending from the cable cross over point 131 at the tendon back plate 105, traveling along the back plate through one or more guides, toward the metacarpal shell 102, through additional guides in the metacarpal shell (e.g., a metacarpal shell cable guide), before returning along the same path on the opposite side of the brace. The radius control loop is formed in a similar fashion, extending from the cross over point 131 through one or more guides in the back plate 105 toward the radius shell 104 and, in some embodiments, entering the adjustment mechanism 106/107.

Each shell may include a cushion section to provide a degree of padding between the more ridged plate and the user's arm, wrist, and hand. In various embodiments, the cushion section can also be constructed out of a material in order to reduce movement of the device by providing a high degree of static friction between the material and the user. In various embodiments, the cushion section may conform nearly identically to the plate. In other embodiments, the cushion section may extend well beyond the plate, and may provide additional benefits or features, such as mounting holes, restraints, or a location for guides.

Figure 22:
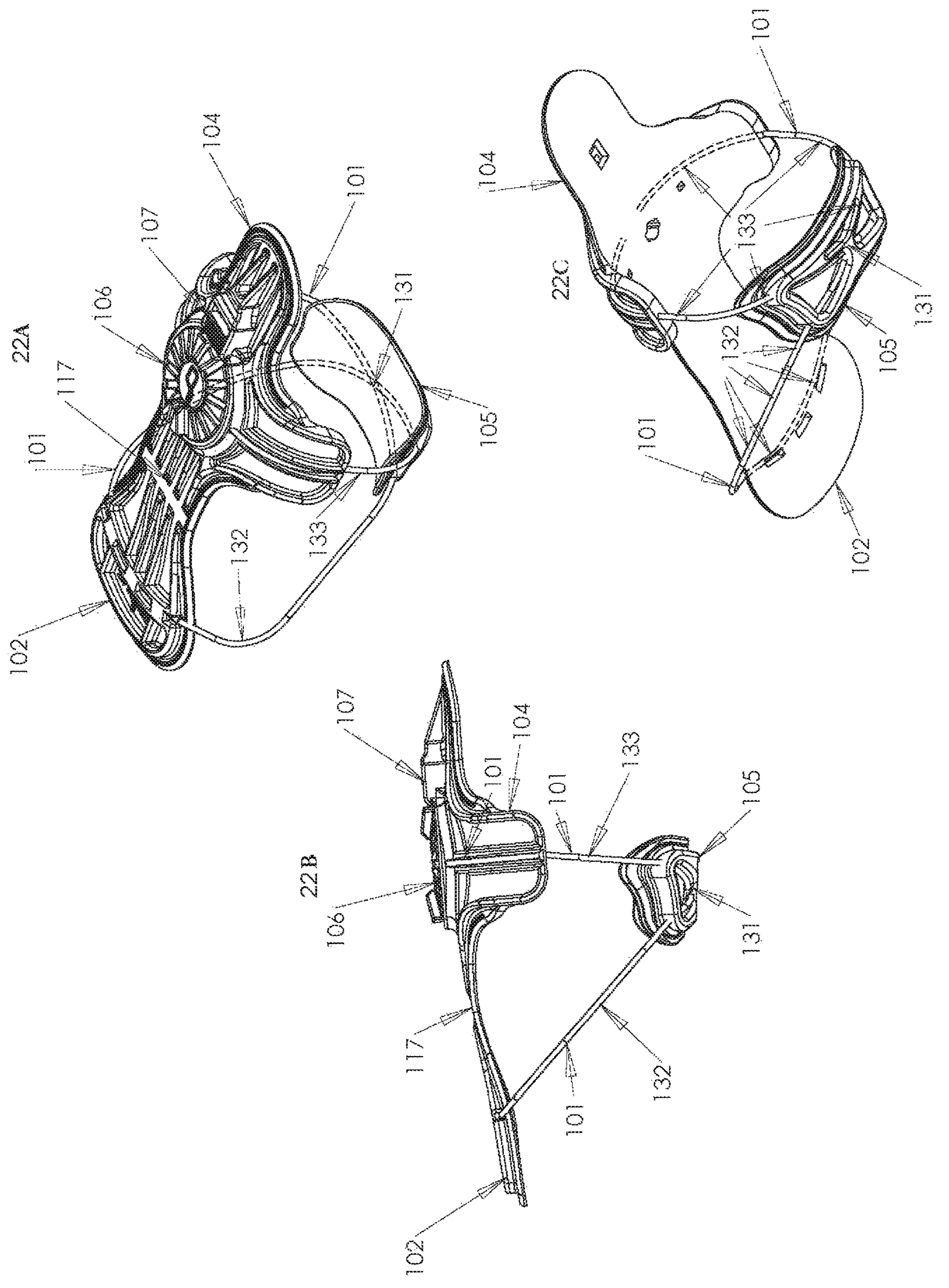
FIG. 22A-C provides multiple views of wrist brace embodiments of the present invention.

FIG. 22 shows the routing of cable 101 beginning attached to the radius shell 104, then passing through the tendon back plate 105, over and through the metacarpal shell 102, back through the tendon back plate 105 crossing over itself, back up to and attaching to the opposite side of the radius shell 104.

Figure 20:
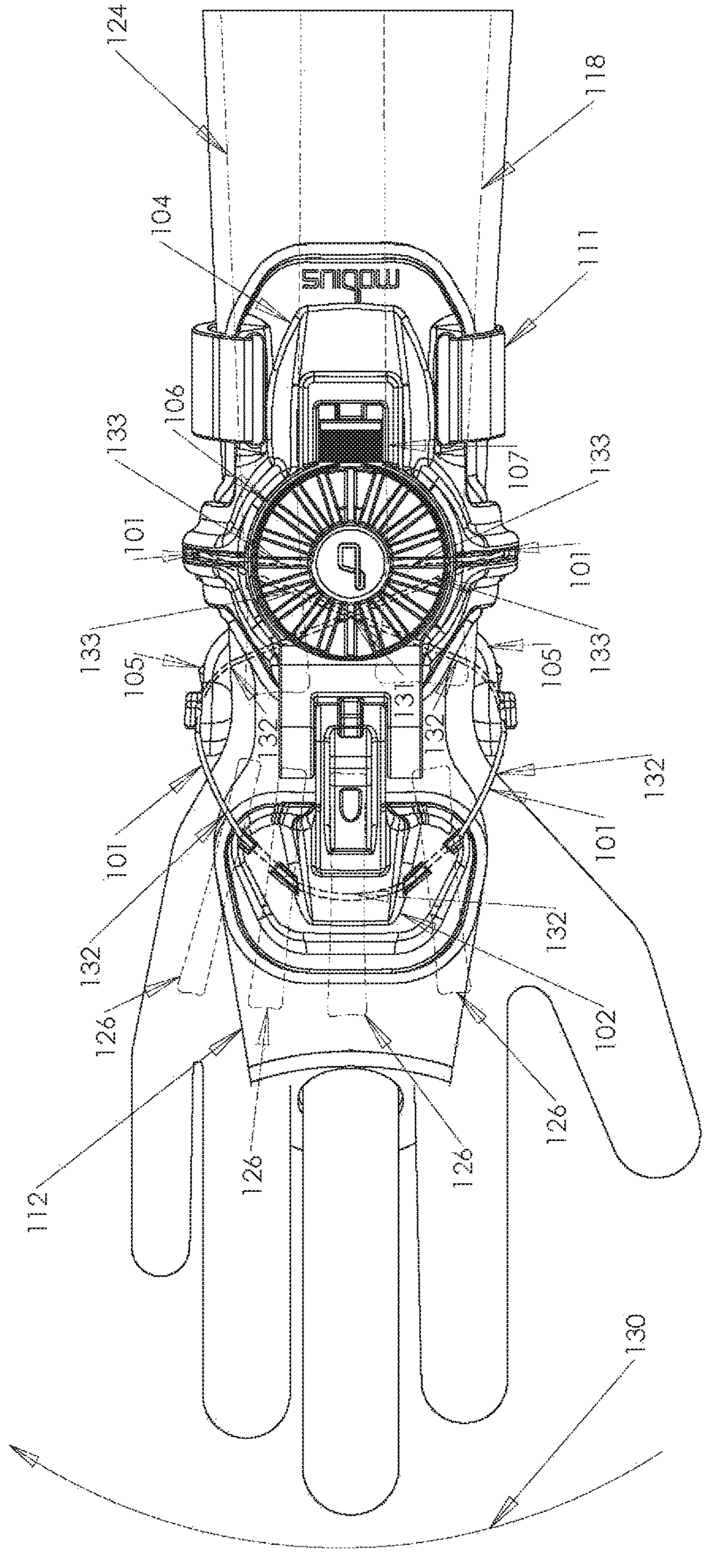
FIG. 20 is a top view of a wrist brace on a right wrist consistent with the embodiment of the present invention.

The cable system also provides progressive support, such that, as the user's wrist is subjected to a lateral bending or rotation force 130 as shown in FIG. 20, increased bending and or rotation is met with increased restriction.

Figure 19:
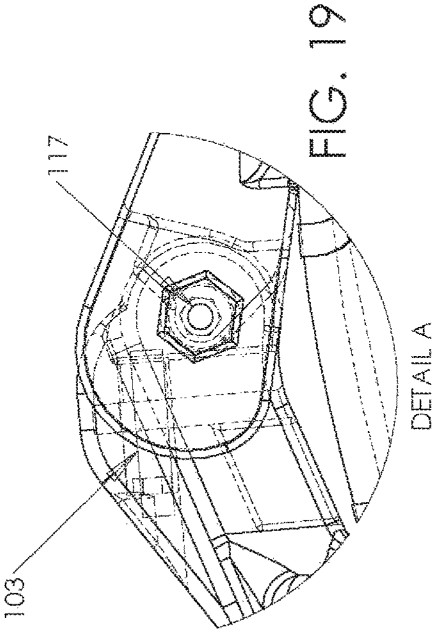
FIG. 19 provides a detail view of an extension stop mechanism for the wrist brace consistent with the embodiment of the present invention.

As depicted in FIGS. 18 and 19, the radius shell 104 can be connected to the metacarpal shell 102 at least one point 117. Preferably, the point at which the connection is made is allowed to pivot as shown. This pivot can be adjusted with adjustment screw 103 to provide for a specified amount of movement, or alternatively, it may be locked to prevent movement. The pivot may be controlled in one or both of degree of movement, as well as resistance. In additional embodiments, the metacarpal plate may not be hinged at all, and instead, may be constructed of a material with a natural spring, as shown in FIG. 22, such that some movement of the user's hand is allowed in the upward direction, but that movement is met with increased force as the spring tension (desire of the material to return to its original form) increases.

As depicted in FIG. 18, the radius shell 104 can be connected to the metacarpal shell 102 at least one point forming one piece. Preferably, the point at which the connection is made forms a hinge point 117 and is allowed to pivot as shown.

Various additional attachment mechanisms may be employed. For example, as depicted, a strap 111 may be included, or not at all as shown in FIG. 22. As depicted in FIGS. 18 and 20 the soft liner 112 may extend over one or more of the user's fingers in order to provide increased stability to the device. In various embodiments, additional straps may be included toward the back of the brace and toward the upper arm. In other embodiments, additional straps may be used, or in place of the finger holes in the liner 112.

The semi-rigid shells are formed such that they engage the user's bones, radius 118, ulna 124, and Metacarpus 126 through the skin, in a manner that aids in their rigidity with respect to movement during use. By properly engaging the bone, there is less deflection due to skin, fat, or other tissue.

Figure 21:
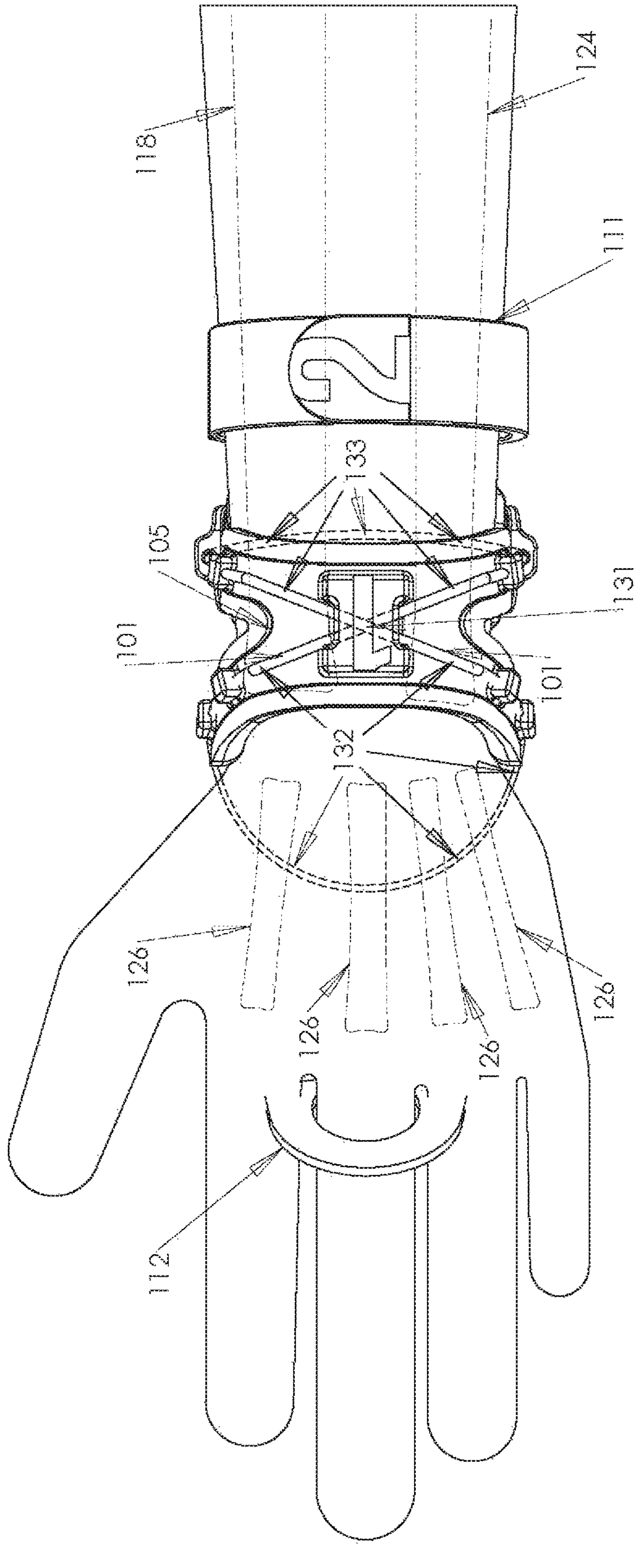
FIG. 21 is a bottom view of a wrist brace consistent with the embodiment of the present invention.

FIG. 21 illustrates a tendon back plate 105 according to an embodiment of the present invention. The tendon back plate 105 may include a number of guides to control the movement of the cable system. For example, the depicted embodiment includes four areas where the cable first comes into contact with the tendon back plate. Additional guides may be used. In addition, depending on the configuration, various embodiments may include a guide where the cable system crosses over at cross over point 131. For example, the depicted embodiment includes a central guide that allows the cable to cross as the cables extend diagonally. In other embodiments, the cables may not cross, and may simple run close to one another, and additional or different guides may be used. Further, the depicted embodiment is shaped such that the outward portions of the back plate 105 extend up toward the upper shells 102 and 104.

While the tendon back plate 105 preferably is shaped to ergonomically conform to the contours of the lower wrist, arm, and palm, the shape is not so limited. Further, additional plates or components, for example, a hinged portion toward the hand which supports the hand, may be added. Or, in alternative embodiments, the back plate 105 may be composed of two or more plates. For example, the depicted embodiments may be composed of three discrete plates, one for the forward guides, one for the central guide, and another for the rearward guides. Many additional configurations are possible and contemplated herein.

FIG. 21 also depicts the routing of the cables creates two separate control portions, 132 and 133, each on their respective side of cable cross over point 131. The loops appear in other figures as well. The metacarpal control loop 132 extends from the cable cross over point up and over the metacarpal shell 102, returning to the cable cross over point 131 at the other side. The radius control loop 133 extends from cable cross over point 131 up and over the rear portion, away from the hand, of the radius shell 104, returning to cable cross over point 131. In use, the lengths or the control loops 132 and 133 are inversely related. For example, if a user's wrist is bent, lengthening metacarpal control loop 132, radius control loop 133 shortens, this shortening draws the back plate 105 and the radius plate 104 together, stopping further lengthening of metacarpal control loop 132 and thereby preventing hyperextension.

The routing of the cables may change depending on the embodiment of the present invention. For example, where the hinged portion, the metacarpal shell, is fixed as depicted in FIG. 22A-C, the routing may be moved forward or rearward. Additionally, in some embodiments, there may be more than one adjustment mechanism. For example, there may be a forward and a rearward mechanism.

While the invention has been described and illustrated with regard to the particular embodiment, changes and modifications may readily be made, and it is intended that the claims cover any changes, modifications, or adaptations that fall within the spirit and scope of the invention.

Ankle Brace

In addition to the embodiments described above. Another embodiment of the present invention provides support for a user's ankle. The ankle brace embodiment incorporates many of the features described herein for alternative ligament braces.

Figure 25:
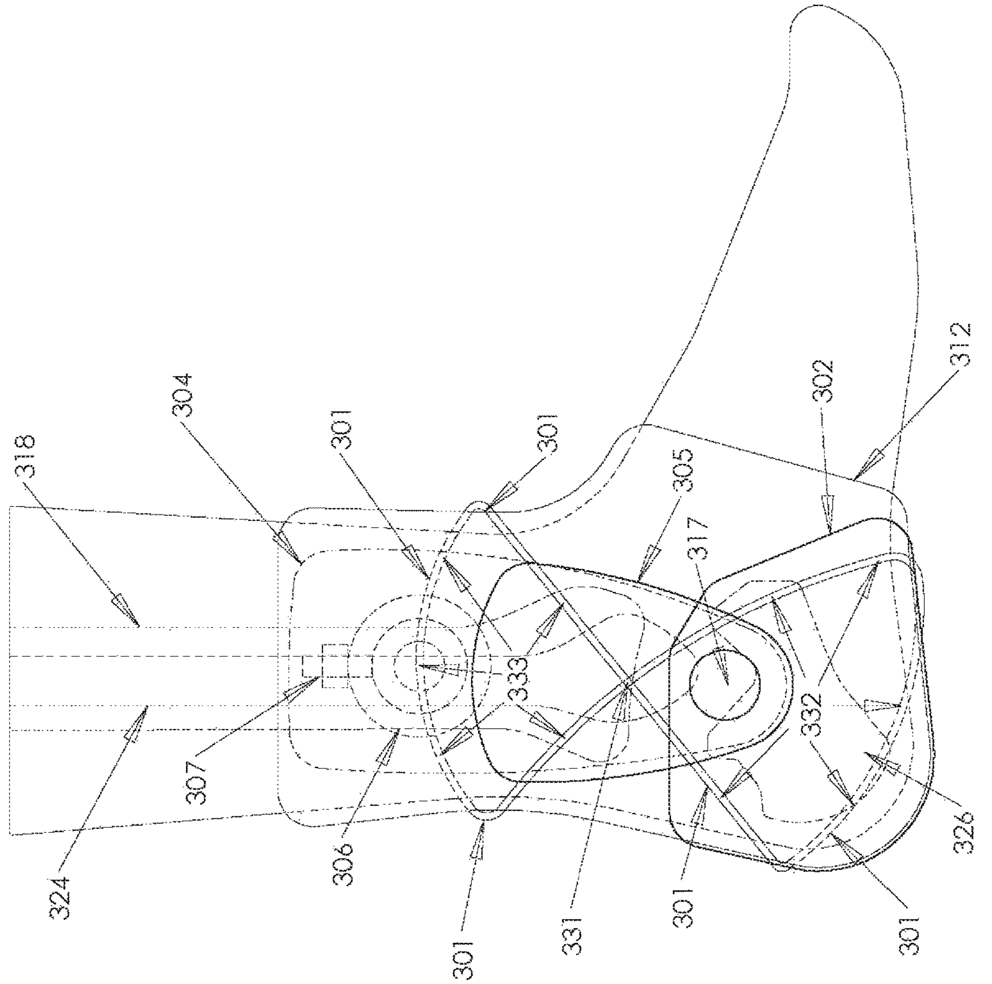
FIG. 25 is an outside elevation/side view of an ankle brace on a right foot consistent with the embodiment of the present invention.
Figure 26:
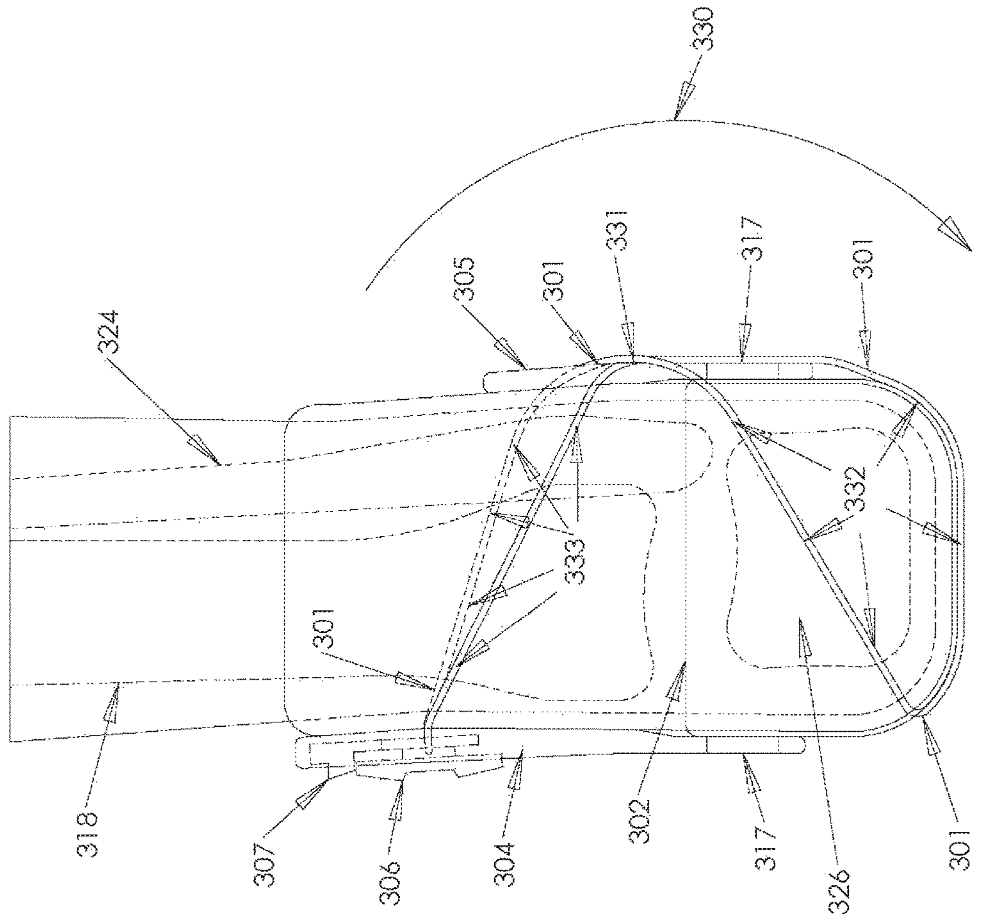
FIG. 26 is a back view of an ankle brace on a right foot consistent with the embodiment of the present invention.

As depicted at FIGS. 25-26, a brace is shown which can stabilize a user's ankle, preventing lateral bending. As depicted, an ankle brace combines a soft boot type portion with a plurality of semi rigid shells. The portions of the semi-rigid shells are preferably a fibula 305, tibial 304, and calcaneus 302 shells. An adjustment mechanism 306 can be located on the tibial shell 304, or optionally on any other shell. The adjustment mechanism 306 allows for tightening of cable(s) 301. The cable 301 engages the fibula 305, tibial 304, and calcaneus 302 shells, and when tightened, brings the shells toward one another. The cable system also provides progressive support, such that, as the user's ankle bends, increase bending is met with increased restriction.

As with other embodiments, two control loops are formed, an upper loop 333 and a lower loop 332. These loops work in concert to prevent unwanted ankle movement, for example, as lower loop 332 extends (as the ankle bends) the upper loop 333 shortens, pulling the shell 304 and 305 into the leg. This in turn prevents the lower loop 332 from allowing the ankle/foot to continue its movement, thereby lateral bending.

The cable system may be routed in a number of ways. For example, the cable may cross, forming cross over point 331, at the fibula shell 305, and loop at both the tibial shell 304 and the calcaneus shell 302.

As depicted in FIG. 25, the fibula shell 305 can be connected to the calcaneus shell 302 at a pivot point 317. Preferably, the point at which the connection is made is allowed to pivot. This pivot 317 can be adjusted to provide for a specified amount of movement, or alternatively, it may be locked to prevent movement.

The semi-rigid shells are formed such that they engage the user's bones 318, 324, and 326, through the skin, in a manner that aids in their rigidity with respect to movement during use. By properly engaging the bone, there is less deflection due to skin, fat, or other tissue. The cable 301 and control loops 332 and 333 assist by directing force toward the bones from the points around the loop, stabilizing the brace itself, which further increases its effectiveness.

While the invention has been described and illustrated with regard to the particular embodiment, changes and modifications may readily be made, and it is intended that the claims cover any changes, modifications, or adaptations that fall within the spirit and scope of the invention.

Elbow Brace

The brace systems described above, and their novel control loop systems, can be adapted to the elbow to prevent the arm from hyperextending.

In such an embodiment, as compared to the knee brace described above, a humorous plate 204 would substitute for the femoral plate 4, an ulna plate 202 would substitute for the tibial plate 2, and bicep plate would substitute for the femoral back plate 5 creating the differential resistive force across the elbow joint preventing hyperextension of the arm. In much the same way as the embodiments described herein, two control loops are created, each extending from a cross over point 231, an ulna control loop 232 and a humorous control loop 233.

Figure 23:
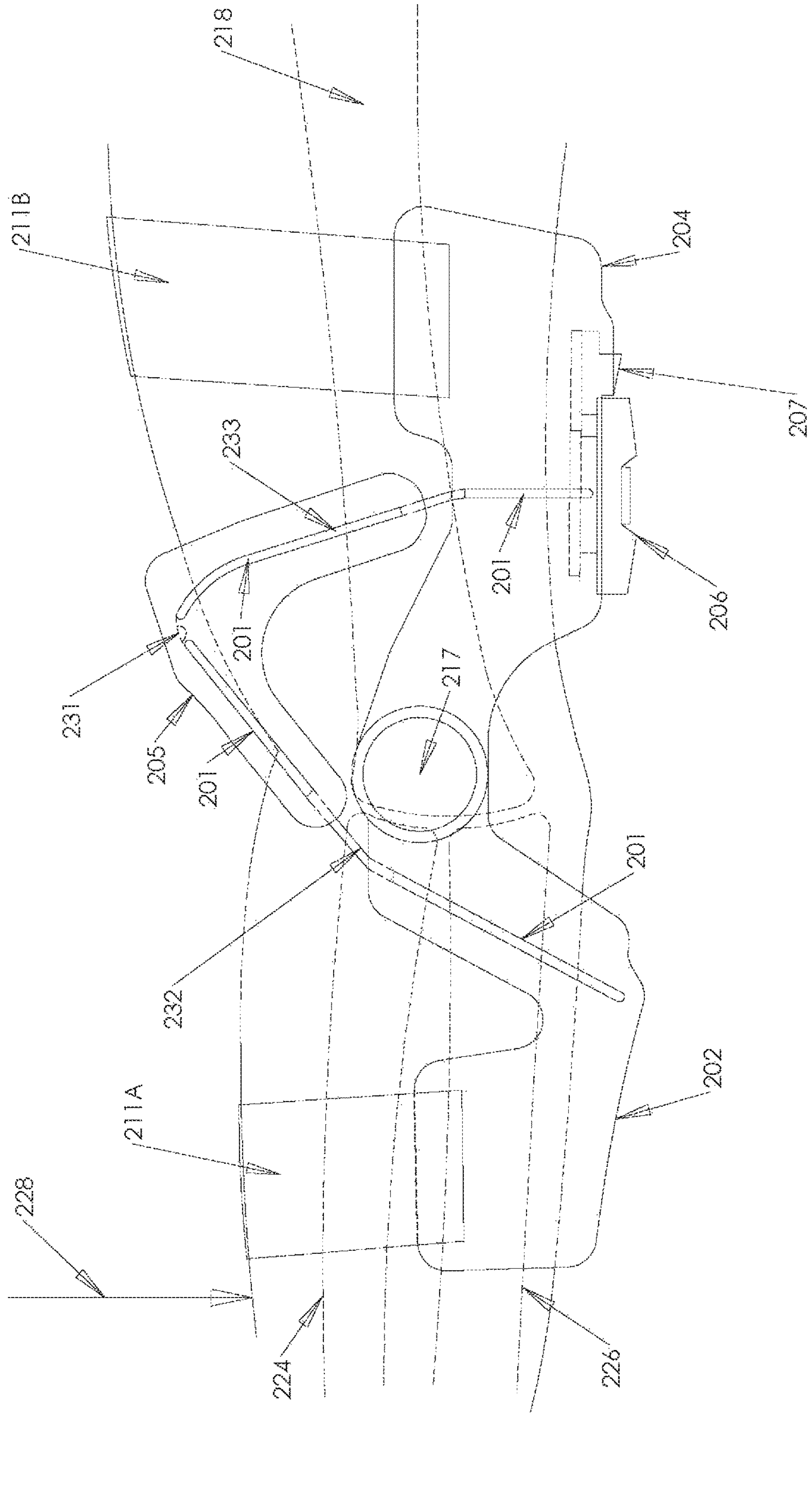
FIG. 23 is an inside elevation/side view of an elbow brace on a right elbow consistent with an embodiment of the present invention.
Figure 24:
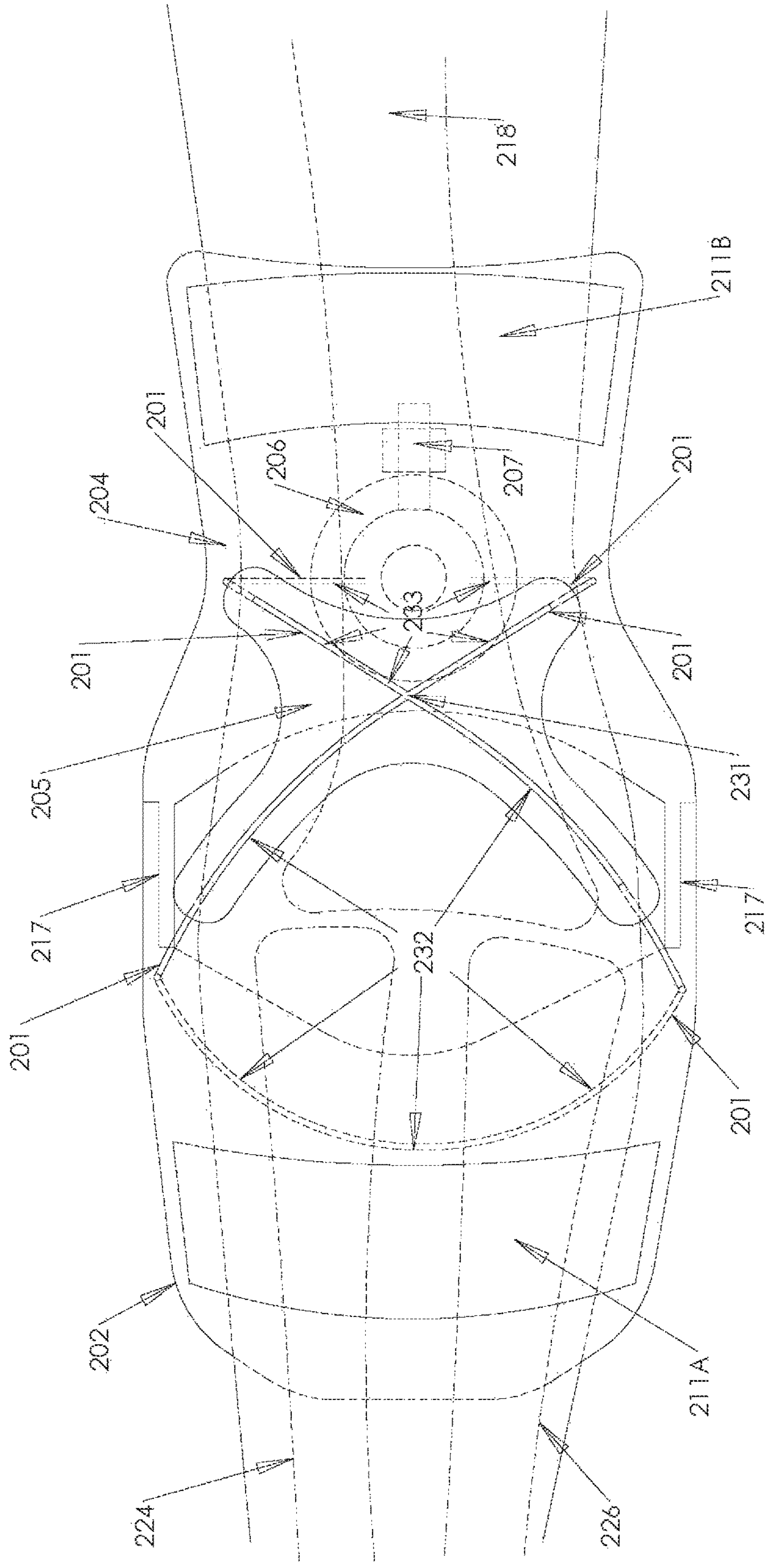
FIG. 24 is a top view of an elbow brace on a right elbow consistent with an embodiment of the present invention.

As depicted at FIGS. 23 and 24, a brace is shown which can stabilize a user's elbow, preventing hyperextension. As depicted, an elbow brace is comprised of semi rigid shells, preferably a humerus shell 204, ulna shell 202, and tendon back plate 205. An adjustment mechanism can be located on the humerus shell 204, or optionally on any other shell. The adjustment mechanism dial 206 and ratchet 207 allows for tightening of a cable system. The cable 201 engages the ulna shell 202, humerus shell 204, and tendon back plate 205, and when tightened, brings the shells toward one another.

The cable system also provides progressive support, such that, as the user's elbow is subjected to a hyperextension force 228, increased extension is met with increased restriction. For example, as the user's elbow extends, control loop 232 lengthens. In response, control loop 233 shortens, this shortening pulls the back plate 205 and humerus shell 204 toward the arm, resisting and then stopping any further extension of the control loop 232 and thereby preventing hyperextension. The cable system also benefits from these loops because the tightening force is directed toward the center of the arm from every point around the loop. This provides better brace stability, and as a result, better control of the arm's movement. FIG. 24 depicts these loops with the aid of arrows showing their positions surrounding the user's arm.

As depicted in FIG. 23, the ulna shell 202 can be connected to the humerus shell 204 at least one point 217. Preferably, the point at which the connection is made is allowed to pivot as shown. This pivot can be adjusted to provide for a specified amount of movement, or alternatively, it may be locked to prevent movement.

Various additional attachment mechanisms may be employed. For example, as depicted, a strap 211A-B may be included. In various embodiments, the strap may be included toward the back of the brace and toward the upper arm, 211B. In other embodiments, additional straps may be used such as an ulna strap 211A. For example, another strap may be added to the ulna shell 202 and one or more straps may be added to the humerous shell 204.

The semi-rigid shells are formed such that they engage the user's bones, ulna 226, radius 224, and humerus 218 through the skin, in a manner that aids in their rigidity with respect to movement during use. By properly engaging the bone, there is less deflection due to skin, fat, or other tissue.

While the invention has been described and illustrated with regard to the particular embodiment, changes and modifications may readily be made, and it is intended that the claims cover any changes, modifications, or adaptations that fall within the spirit and scope of the invention.

What is claimed is:

1. A brace adapted for selective interconnection to a user's wrist, comprising:

a radius plate configured to receive a radius portion of an arm and including a tightening strap, the radius plate having a radius plate cable guide;

a metacarpal shell configured to receive a metacarpal portion of a hand, the metacarpal shell being hingedly interconnected to the radius plate, thereby allowing movement of the wrist, the metacarpal shell also having a metacarpal shell cable guide;

a tendon back plate configured to be positioned on an underside of the wrist, and wherein the tendon back plate cooperates with the radius plate and the metacarpal shell, the tendon back plate having a tendon back plate cable guide, wherein the tendon back plate is X-shaped, and configured to begin near the user's palm and extend rearward, with legs of the tendon back plate accommodating the tendon back plate cable guide;

a cable comprised of a substantially inelastic material, wherein the cable is routed from the radius plate, around the tendon back plate, around and over the top of the metacarpal shell, crossing over itself at a crossover point at the tendon back plate, and then back to the top of the radius plate, and wherein the cable is routed through a cable tensioner comprising a tension adjustment dial and a ratchet, and wherein a radius loop portion of the cable, which extends from the crossover point over the radius plate and back to the crossover point, and a metacarpal loop portion of the cable, which extends from the crossover point over the metacarpal shell and back to the crossover point, are configured such that a lengthening of the metacarpal loop portion results in a corresponding shortening of the radius loop portion.

2. The brace of claim 1, wherein the cable tensioner is mounted to the front of the radius plate, and wherein the cable enters and exits from opposing sides of the cable tensioner.

3. The brace of claim 1, wherein the cable is attached to the metacarpal shell.

4. The brace of claim 1, wherein the cable includes cable segments coupled together.

5. The brace of claim 1, wherein differential forces associated with the lengthening and/or contraction of the metacarpal loop portion and/or the radius loop portion urges the tendon back plate closer to the metacarpal shell and closer to the radius plate.

6. The brace of claim 1, wherein a corresponding tightening force resulting from the shortening of the radius loop portion draws the radius plate and the tendon back plate closer together, and provides a radial force along the metacarpal loop portion directed toward the center of the metacarpal loop portion.

7. The brace of claim 1, wherein the radius plate and the metacarpal shell are rigid or semi-rigid.

8. The brace of claim 1, wherein the metacarpal shell includes a portion of material configured to extend over one or more of the user's fingers.

9. The brace of claim 1, wherein the radius plate, metacarpal shell, and tendon back plate include a cushion section configured to make contact with the user's arm.

10. The brace of claim 9, wherein the cushion section extends beyond an area covered by the radius plate and the metacarpal shell.

11. A brace adapted for selective interconnection to a user's wrist, comprising:

a radius plate configured to receive a radius portion of an arm and including a tightening strap, the radius plate having a radius plate cable guide;

a metacarpal shell configured to receive a metacarpal portion of a hand, the metacarpal shell being connected to the radius plate without being hinged thereto with a material that functions as a natural spring, wherein the brace is configured to allow movement of a user's hand in one direction, but that movement is met with increased force as a spring tension of the material increases, thereby allowing movement of the wrist, the metacarpal shell also having a metacarpal shell cable guide;

a tendon back plate configured to be positioned on an underside of the wrist, and wherein the tendon back plate cooperates with the radius plate and the metacarpal shell, the tendon back plate having a tendon back plate cable guide;

a cable comprised of a substantially inelastic cable material, wherein the cable is routed from the radius plate, around the tendon back plate, around and over the top of the metacarpal shell, crossing over itself at a crossover point at the tendon back plate, and then back to the top of the radius plate, and wherein the cable is routed through a cable tensioner comprising a tension adjustment dial and a ratchet;

and wherein a radius loop portion of the cable, which extends from the crossover point over the radius plate and back to the crossover point, and a metacarpal loop portion of the cable, which extends from the crossover point over the metacarpal shell and back to the crossover point, are configured such that a lengthening of the metacarpal loop portion results in a corresponding shortening of the radius loop portion.

12. The brace of claim 11, wherein the cable tensioner is mounted to the front of the radius plate, and wherein the cable enters and exits from opposing sides of the cable tensioner.

* * * * *